United States Patent
Uckun et al.

(10) Patent No.: US 6,316,454 B1
(45) Date of Patent: Nov. 13, 2001

(54) 6,7-DIMETHOXY-4-ANILINOQUINAZOLINES

(75) Inventors: Fatih M. Uckun, White Bear Lake; Rama Krishna Narla, St. Paul; Xing-Ping Liu, Minneapolis, all of MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/361,088

(22) Filed: Jul. 26, 1999

Related U.S. Application Data

(63) Continuation of application No. 09/087,479, filed on May 28, 1998.

(51) Int. Cl.⁷ .................... C07D 239/94; A61K 31/517; A61P 35/00
(52) U.S. Cl. ............................. 514/259; 544/293
(58) Field of Search ............. 514/259; 544/283, 544/293

(56) References Cited

U.S. PATENT DOCUMENTS

| | | | |
|---|---|---|---|
| 4,343,940 | 8/1982 | Kreighbaum et al. | 544/283 |
| 5,457,105 | * 10/1995 | Barker | 514/234.5 |

(List continued on next page.)

FOREIGN PATENT DOCUMENTS

| | | |
|---|---|---|
| 29 36 705 A1 | 3/1980 | (DE) . |
| 0 566 226 A1 | 10/1993 | (EP) . |

(List continued on next page.)

OTHER PUBLICATIONS

Bridges, A. et al., "Tyrosine Kinase Inhibitors. 8. An Unusually Steep Structure—Activity Relationship for Analogues of 4–(3–Bromoanilino)–6,7–dimethoxyquinazoline (PD 153035), a Potent Inhibitor of the Epidermal Growth Factor Receptor", *Journal of Medicinal Chemistry*, vol. 39, pp. 267–276 (1996).

(List continued on next page.)

*Primary Examiner*—Mukund J. Shah
*Assistant Examiner*—Thomas McKenzie
(74) *Attorney, Agent, or Firm*—Merchant & Gould, P.C.

(57) ABSTRACT

6,7-Dimethoxy-4-anilinoquinaozolines of the formula:

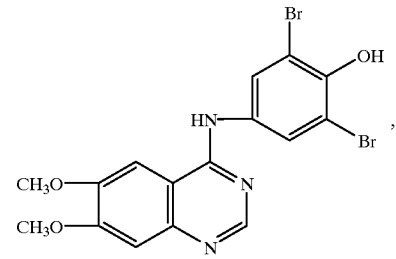

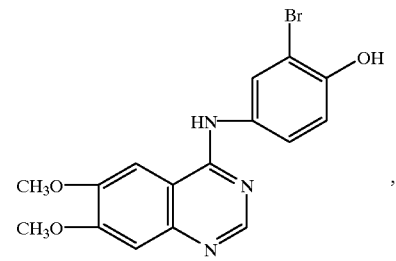

or pharmaceutically acceptable acid addition salts thereof are disclosed. These novel compounds are useful for inducing apoptosis and preventing metastases of brain tumor cells.

15 Claims, 16 Drawing Sheets

U.S. PATENT DOCUMENTS

| | | | |
|---|---|---|---|
| 5,480,883 | * | 1/1996 | Spada et al. .......................... 514/249 |
| 5,710,158 | * | 1/1998 | Myers et al. .......................... 514/259 |
| 5,714,493 | * | 2/1998 | Myers et al. .......................... 514/259 |
| 5,721,237 | * | 2/1998 | Myers et al. .......................... 514/259 |
| 5,792,771 | | 8/1998 | App et al. ............................ 514/259 |

FOREIGN PATENT DOCUMENTS

| | | | |
|---|---|---|---|
| EP0566226 A1 | * | 10/1993 | (GB) . |
| WO 95/15758 | * | 6/1995 | (WO) . |
| WO 96/09294 | * | 3/1996 | (WO) . |
| WO 96/15118 | | 5/1996 | (WO) . |
| WO 96/40648 | | 12/1996 | (WO) . |
| WO 96/39145 | * | 12/1996 | (WO) . |
| WO 97/30035 | * | 8/1997 | (WO) . |
| WO 97/32856 | * | 9/1997 | (WO) . |

OTHER PUBLICATIONS

Budesinsky, Z. et al., "A New Synthesis of the Quinazoline Nucleus", *Collection of Czechoslovak Chemical Communications*, vol. 37, No. 8, pp. 2779–2785 (Aug. 1972).

Fetter, J. et al., "Electron Deficient Heteroaromatic Ammonioamidates–XVI*a*, The Synthesis and Photochemistry of Ethyl N–(2–Methyl–4–Methylene–6,7–Methylenedioxy–3, 4–Dihydro–3–Quinazolinyl)–N–Phenylcarbamate", *Tetrahedron*, vol. 34, pp. 2557–2563 (1978).

Goodman, P. et al., "Role of Tyrosine Kinases in Induction of the c–jun Proto–oncogene in Irradiated B–lineage Lymphoid Cells", *The Journal of Biological Chemistry*, vol. 273, No. 28, pp. 17742–17748 (Jul. 10, 1998).

Higashino, T. et al., "Reactions of the anion of quinazoline Reissert compound (3–benzoyl–3, 4–dihydro–4–quinazolinecarbon itrile) with electrophiles", *Chemical & Pharmaceutical Bulletin*, vol. 33, No. 3, pp. 950–961 (Mar. 1985).

Ife, R. et al., "Reversible Inhibitors of the Gastric (H+/K+)–ATPase", *Journal of Medicinal Chemistry*, vol. 38, No. 14, pp. 2763–2773 (Jul. 7, 1995).

Kubo, K. et al., "A Novel Series of 4–Phenoxyquinolines: Potent and Highly Selective Inhibitors of PDGF Receptor Autophosphorylation", *Bioorganic & Medicinal Chemistry Letters*, vol. 7, No. 23, pp. 2935–1940 (Dec. 2, 1997).

Malaviya, R et al., "Genetic and Biochemical Evidence for a Critical Role of Janus Kinase (JAK)–3 in Mast Cell–Mediated Type I Hypersensitivity Reactions", *Biochemical and Biophysical Research Communications*, vol. 257, No. 3, pp. 807–813 (Apr. 21, 1999).

Miyashita, A. et al., "An Approach to the Synthesis of a Papaverine Analogue Containing a Quinazoline Ring System", *Heterocycles*, vol. 40, No. 2, pp. 653–660 (1995).

Nomoto, Y. et al., "Studies on Cardiotonic Agents. I. Synthesis of some Quinazoline Derivatives", *Chemical and Pharmaceutical Bulletin*, vol. 38, No. 6, pp. 1591–1595 (1990).

* cited by examiner

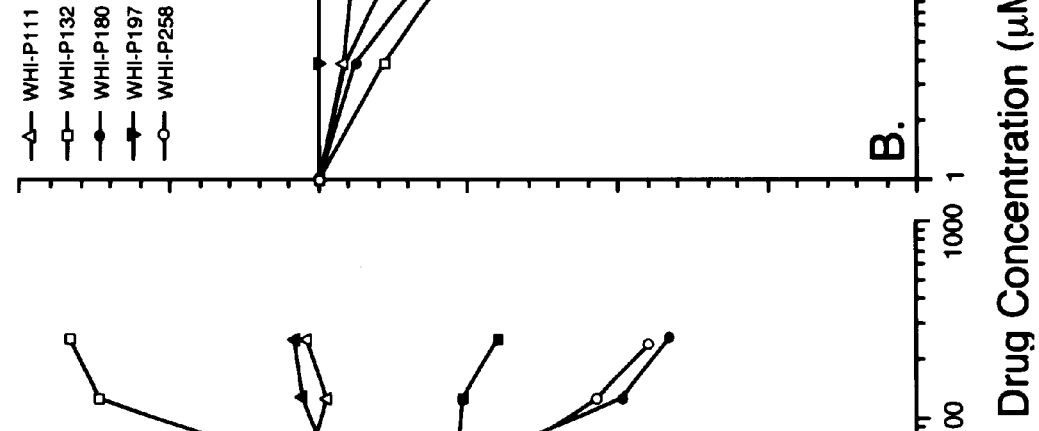
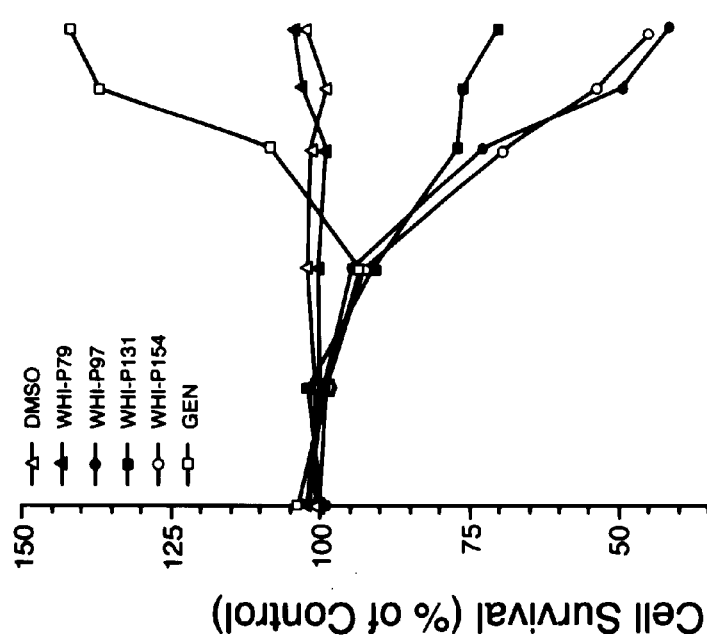

6,7-DIMETHOXY-4-ANILINOQUINAZOLINES

This application is a continuation of U.S. Ser. No. 09/087,479, filed May 28, 1998, which application is incorporated by reference herein.

FIELD OF THE INVENTION

This invention relates to novel quinazoline derivatives effective to induce apoptosis of brain tumor cells. In particular, the invention includes novel hydroxy quinazoline derivatives having potent cytotoxicity against human brain tumor cells, including glioblastoma. The novel compounds of the invention further inhibit adhesion of brain tumor cells to extracellular matrix proteins and inhibit migration of brain tumor cells through the extracellular matrix, activities required for tumor metastases.

BACKGROUND OF THE INVENTION

As the most malignant primary central nervous systems tumors, high grade anaplastic astrocytoma and glioblastoma multiforme respond poorly to contemporary multimodality treatment programs employing surgical resection, radiation therapy and chemotherapy with a median survival of less than one year after initial diagnosis (Pardos, et al., 1997, *Cancer Medicine*, 1:1471–1514; Brandes, et al., 1996, *Cancer Invest.* 14:551–559; Finlay, J. L., 1992, Pediatric Neuro-Oncology, 278–297; Pardos, et al., 1998, *Sem. Surgical Oncol.*, 14:88–95). Consequently, the development of effective new agents and novel treatment modalities against these very poor prognosis brain tumors remains a major focal point in translational oncology research.

Glioblastoma multiforme is also a highly invasive primary brain tumor with a disappointingly high local recurrence rate and mortality. New agents capable of inhibiting the infiltration of normal brain parenchyma by glioblastoma cells are urgently needed.

SUMMARY OF THE INVENTION

In a systematic effort to identify a cytotoxic agent with potent anti-tumor activity against glioblastoma cells, several hydroxy-substituted quinazoline-derivatives were synthesized and examined for their in vitro and in vivo effects on human glioblastoma cells. Novel hydroxy- and halo-hydroxy-quinazoline derivatives were found to exhibit potent cytotoxic activity against human glioblastoma cells at micromolar concentrations. Targeting of these compounds to the surface of brain tumor cells, for example, by conjugating hydroxy- and the halo-hydroxy compounds to a targeting moiety such as epidermal growth factor (EGF), further enhanced the cytotoxic activity (at nanomolar concentrations). The conjugate demonstrated more rapid and more potent anti-brain tumor activity, including apoptotic death of glioblastoma cells in vitro, significantly improved tumor-free survival in an in vivo SCID mouse glioblastoma xenograft model, inhibition of tumor cell adhesion to ECM proteins, and inhibition of tumor cell migration and invasion activity.

Accordingly, the present invention includes novel compounds and compositions having potent cytotoxic activity against brain tumor cells. Compositions of the invention contain an effective cytotoxic or inhibitory amount of a hydroxy-substituted quinozaline compound, more particularly of a hydroxy- or halo-hydroxy-substituted quinazoline derivative. The compounds of the invention include those having the following formula:

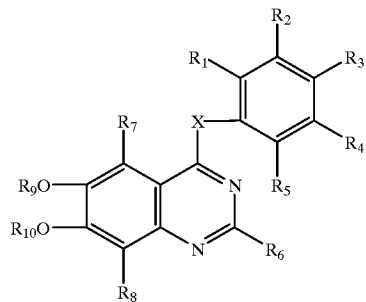

where X is HN, $R_{11}N$, S, O, $CH_2$, or $R_{11}CH$, and one or more of $R_1$, $R_2$, $R_3$, $R_4$, $R_5$ is OH, SH, or $NH_2$. Preferred embodiments include those where X is HN; $R_3$ is OH; $R_2$ and/or $R_4$ is a halogen, preferably Br. In another preferred embodiment, one or more of $R_1$-$R_5$ form a second ring fused to the phenyl ring, for example, forming a napthyl ring and having at least one hydroxy substitution.

Preferred cytotoxic compounds of the invention include 4-(3'-Bromo-4'-hydroxymethyl)-amino-6,7-dimethoxyquinazoline [WHI-P154], 4-(4'-Hydroxylphenyl)-amino-6,7-dimethoxyquinazoline [WHI-P131], and 4-(2'-Hydroxy-naphthyl-3')-amino-6,7-dimethoxyquinazoline [WHI-P292].

The compounds of the invention can be formulated for delivery to a subject as a pharmaceutical composition, and can preferably be modified for selective killing of brain tumor cells by conjugation to a cell specific targeting moiety, such as an anti-cell surface antigen-antibody, or a moiety known to bind a cell surface receptor, such as EGF. The compounds of the invention are preferably covalently bonded to the targeting moiety. One exemplary targeting moiety is EGF, which, when conjugated to the compound of the invention, rapidly and specifically directs the compound to brain tumor cells expressing the EGF receptor, resulting in specific, rapid, and enhanced cytotoxicity.

The compounds of the invention are administered to a subject to inhibit the growth of brain tumor cells, to induce apoptosis of brain tumor cells, thereby reducing tumor mass. Compounds of the invention are also administered to inhibit the adhesion and migration of brain tumor cells, for example, inhibiting the infiltration of normal brain parenchyma by glioblastoma cells.

BRIEF DESCRIPTION OF THE DRAWINGS

FIGS. 1A and 1B are cell survival graphs demonstrating the cytotoxic activity of WHI-P154 and other compounds of the invention against U373 glioblastoma cells.

DETAILED DESCRIPTION OF THE INVENTION

Figure 2A:
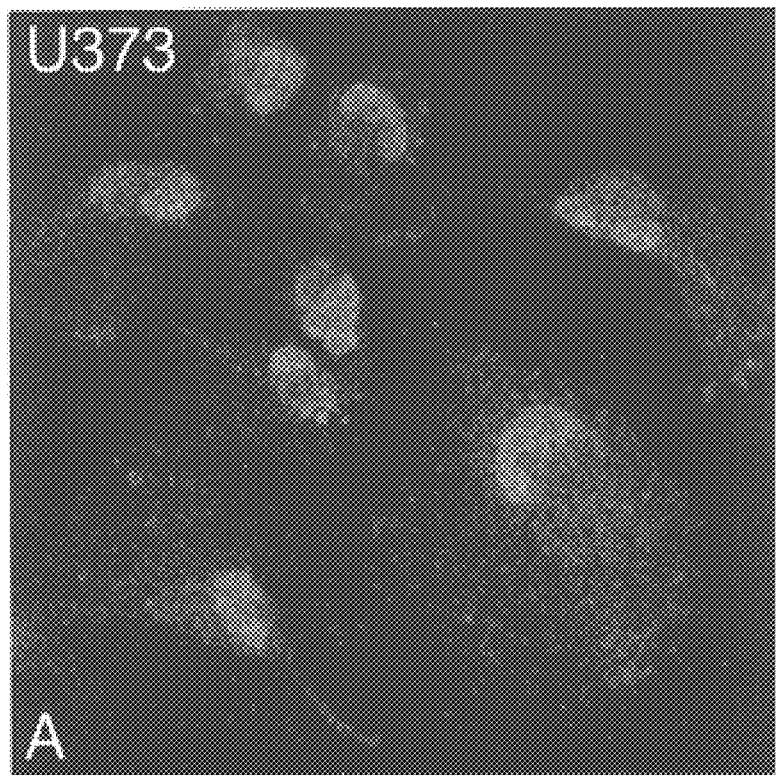
FIGS. 2A and 2B are photographs of laser analyzed immunostained cells demonstrating cell surface expression of EGF receptor on U373 and U87 human glioblastoma cells.

The present invention includes novel hydroxy-substituted quinazoline derivatives having potent activity as cytotoxic agents against brain tumor cells, including glioblastoma cells. In addition, the hydroxy-substituted quinazoline compounds of the invention are potent inhibitors of tumor cell adhesion and migration, activities required for tumor cell metastases.

Definitions

All scientific and technical terms used in this application have meanings commonly used in the art unless otherwise specified. As used in this application, the following words or phrases have the meanings specified.

As used herein, "alkyl" includes both branched and straight-chain saturated aliphatic hydrocarbon groups having the specified number of carbon atoms. As a preferred embodiment, chains of 1 to 4 carbon atoms are included, for example methyl, ethyl, propyl, isopropyl, butyl, secondary butyl, t-butyl, and the like.

As used herein, "alkene" includes both branched and straight-chain unsaturated aliphatic hydrocarbon groups having the specified number of carbon atoms, preferably chains of 1 to 4 carbon atoms.

As used herein, "acyl" includes —C(O)R, where R is H, alkyl, or aryl containing 1 to 4 carbon atoms.

As used herein "halogen" includes fluoro, chloro, bromo, and iodo. A preferred halogen or halo substituent is Br.

As used herein, "pharmaceutically acceptable carrier" includes any material which, when combined with a compound of the invention, allows the compound to retain biological activity, such as the ability to induce apoptosis of brain tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

Compounds of the Invention

The novel substituted quinazolines of the invention have the general structure represented by the following formula I:

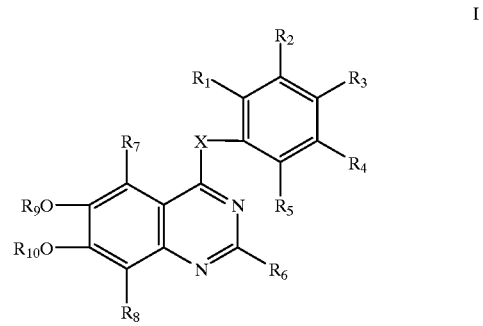

where X is selected from the group consisting of HN, $R_{11}N$, S, O, $CH_2$, and $R_{11}$—CH. $R_{11}$ is H, alkyl, having 1 to 4 carbon atoms, or acyl. Preferably, X is NH; and preferably $R_{11}$ is H.

$R_1$, $R_2$, $R_3$, $R_4$, $R_5$, $R_6$, $R_7$ and $R_8$ are each independently selected from the group consisting of H, OH, SH, $NH_2$, NO2, alkoxy, alkylthio and halogen. $R_9$ and $R_{10}$ are each independently selected from the group consisting of H, alkyl or acyl, containing up to 4 carbon atoms. Preferably, $R_9$ and $R_{10}$ are methyl.

At least one of $R_1$, $R_2$, $R_3$, $R_4$, $R_5$ is OH. Alternatively, at least one of $R_1$ —$R_5$ is a compound such as SH or $NH_2$.

In an alternative embodiment, one or more of $R_1$–$R_5$ forms a second ring fused to the phenyl ring. For example, the following compounds include second rings fused to the phenyl ring via one or more of $R_1$–$R_5$:

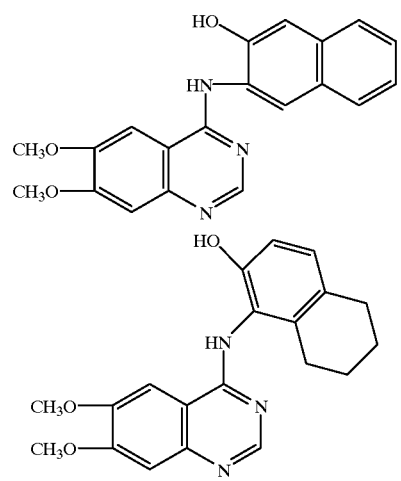

-continued

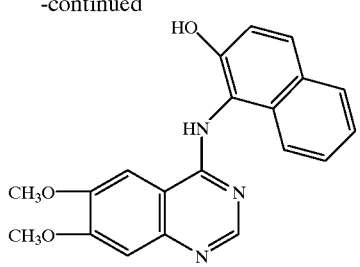

Exemplary Compounds

Some exemplary compounds of the invention are listed below with their characterization data:

4-(3',5'-Dibromo-4'-hydroxylphenyl)-amino-6,7-dimethoxyquinazoline [WHI-P97]

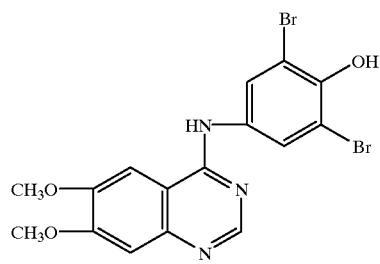

yield 72.80%; m.p.>300.0° C. UV(MeOH)$\lambda_{max}$: 208.0, 210.0, 245.0, 320.0 nm; IR(KBr)$\nu_{max}$: 3504(br), 3419, 2868, 1627, 1512, 1425, 1250, 1155 cm$^{-1}$; $^1$H NMR(DMSO-d$_6$): δ9.71(s, 1H, —NH), 9.39(s, 1H, —OH), 8.48(s, 1H, 2-H), 8.07(s, 2H, 2', 6'-H), 7.76(s, 1H, 5-H), 7.17(s, 1H, 8-H), 3.94(s, 3H, —OCH$_3$), 3.91(s, 3H, —OCH$_3$). GC/MS m/z 456(M$^+$+1,54.40), 455(M$^+$, 100.00), 454(M$^+$-1,78.01), 439 (M$^+$-OH, 7.96), 376(M$^+$+1 -Br, 9.76), 375(M$^+$-Br, 10.91), 360(5.23). Anal. (C$_{16}$H$_{13}$Br$_2$N$_3$O$_3$) C, H, N.

4-(3'-Bromo-4'-methylphenyl)-amino-6,7-dimethoxyquinazoline [WHI-P111]

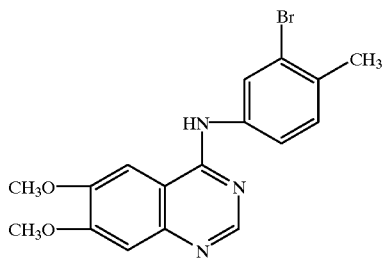

yield 82.22%; m.p.225.0–228° C. $^1$H NMR(DMSO-d$_6$): δ10.23(s, 1H, —NH), 8.62(s, 1H, 2-H), 8.06(D, 1h,j $_{2',6'}$=2.1 Hz. 2'-H), 7.89(s, 1H, 5-H), 7.71(dd, 1H, J$_{5',6'}$=8.7 Hz, J$_{2',6'}$=2.1 Hz, 6'-H), 7.37(d, 1H, J$_{5',6'}$=8.7 Hz, 5'-H, 7.21(s, 1H, 8-H), 3.96(s, 3H, —OCH$_3$), 3.93(s, —OCH$_3$). UV(MeOH)$\lambda_{max}$(ε): 204.0,228.0, 255.0, 320.0 nm. IR(KBr) $\nu_{max}$: 3431, 3248, 2835, 1633, 1517, 1441, 1281, 1155 cm$^{-1}$. GC/MS m/z 375(M$^+$+1, 76.76), 374(M$^+$, 100.00), 373(M$^+$-1, 76.91), 358(M$^+$+1-OH, 11.15), 357(1.42), 356(6.31). Anal. (C$_{17}$H$_{16}$BrN$_3$O$_2$HCl) C, H, N.

4-(4'-Hydroxylphenyl)-amino-6,7-dimethoxyquinazoline [WHI-P131]

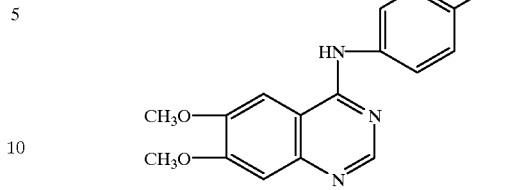

yield 84.29%; m.p. 245.0–248.0.° C. UV(MeOH)$\lambda_{max}$: 203.0, 222.0, 251.0, 320.0 nm; IR(KBr)$\nu_{max}$: 3428, 2836, 1635, 1516, 1443, 1234cm$^{-1}$; $^1$H NMR(DMSO-d$_6$): δ11.21 (s, 1H, —NH), 9.70(s, 1H, —OH), 8.74(s, 1H, 2-H), 8.22(s, 1H, 5-H), 7.40(d, 2H, J=8.9 Hz, 2',6'-H), 7.29(s, 1H, 8-H), 6.85(d, 2H, J=8.9 Hz, 3',5'-H), 3.98(s, 3H, —OCH$_3$), 3.97(s, 3H, —OCH$_3$). GC/MS m/z 298 (M$^+$+1, 100.00), 297(M$^+$, 26.56), 296(M$^+$-1, 12.46). Anal. (C$_{16}$H$_{15}$N$_3$O$_3$HCl) C, H, N.

4-(2'-Hydroxylphenyl)-amino-6,7-dimethoxyquinazoline [WHI-P132]

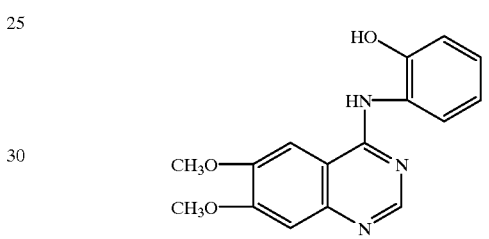

yield 82.49%; m.p. 255.0–258.0° C. $^1$H NMR(DMSO-d$_6$): δ9.78(s, 1H, —NH), 9.29(s, 1H, —OH), 8.33(s, 1H, 2-H), 7.85(s, 1H, 5-H), 7.41–6.83(m, 4H, 3', 4', 5', 6'-H), 7.16(s, 1H, 8-H), 3.93(s, 3H, —OCH$_3$), 3.92(s, 3H, —OCH$_3$). UV(mEoh)$\lambda_{max}$(ε): 203.0, 224.0, 245.0, 335.0 nm. IR(KBr) $\nu_{max}$: 3500 (br), 3425, 2833, 1625, 1512, 1456, 1251, 1068 cm$^{-1}$. GC/MS m/z 298(M$^+$+1, 8.91), 297(M$^+$, 56.64), 281 (M$^+$+1-OH, 23.47), 280(M$^+$-OH, 100.00). Anal. (C$_{16}$H$_{15}$N$_3$O$_3$HCl) C, H, N.

4-(3'-Bromo-4'-hydroxylphenyl)-amino-6,7-dimethoxyquinazoline [WHI-P154]

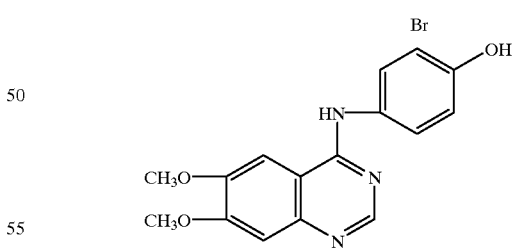

yield 89.90%; m.p. 233.0–233.5° C. UV(MeOH)$\lambda_{max}$: 203.0, 222.0, 250.0, 335.0 nm; IR(KBr)$\nu_{max}$: 3431 br, 2841, 1624, 1498,1423, 1244 cm$^{-1}$; $^1$H NMR(DMSO-d$_6$): δ10.08 (s, 1H, —NH), 9.38(s, 1H, —OH), 8.40(s, 1H, 2-H ), 7.89(d, 1H, J$_{2',5'}$=2.7 Hz, 2'-H), 7.75(s, 1H, 5-H), 7.55(dd, 1H, J$_{5',6'}$=9.0 Hz, J$_{2',6'}$=2.7 Hz, 6'-H), 7.14(s, 1H, 8-H), 6.97(d, 1H, J$_{5',6'}$=9.0 Hz, 5'-H), 3.92(s, 3H, —OCH$_3$), 3.90(s, 3H, —OCH$_3$). GC/MS m/z 378(M$^+$+2, 90.68), 377(M$^+$+1, 37.49), 376(M$^+$, 100.00), 360(M$^+$, 3.63), 298(18.86), 282 (6.65). Anal. (C$_{16}$H$_{14}$N$_3$O$_3$HCl) C, H, N.

4-(3'-Hydroxylphenyl)-amino-6,7-dimethoxyquinazoline [WHI-P180]

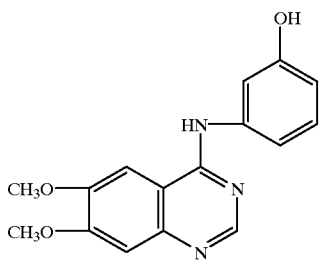

yield 71.55%; m.p. 256.0–258.0° C. $^1$H NMR(DMSO-d$_6$): δ9.41(s, 1H, —NH), 9.36(s, 1H, —OH), 8.46(s, 1H, 2-H), 7.84(s, 1H, 5-H), 7.84–6.50(m, 4H, 2', 4', 5', 6'-H), 7.20(s, 1H, 8-H), 3.96(s, 3H, —OCH$_3$), 3.93(s, 3H, —OCH$_3$). UV(MeOH)λ$_{max}$(ε): 204.0, 224.0, 252.0, 335.0 nm. IR(KBr) ν$_{max}$: 3394, 2836, 1626, 1508, 1429, 1251 cm$^1$. GM/MS m/z: 297(M$^+$, 61.89), 296(M$^+$, 61.89), 296(M$^+$-1, 100.00), 280(M$^+$-OH, 13.63). Anal. (C$_{16}$H$_{15}$N$_3$O$_3$.HCl) C, H, N.

4-(3'-Chloro-4'-Hydroxylphenyl)-amino-6,7-dimethoxyquinazoline [WHI-P197]

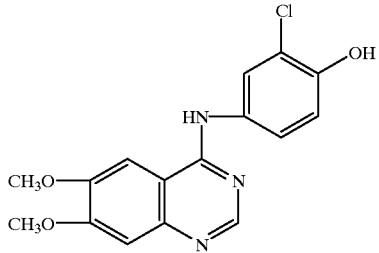

yield 84.14%; m.p. 245.0° C.(dec). $^1$H NMR(DMSO-d$_6$): δ10.00(s, 1H, —NH), 9.37(s, 1H, —OH), 8.41(s, 1H, 2-H), 7.78(s,1H, 5-H), 7.49(d, 1H, J$_{2',6'}$=2.7 Hz, 2'-H), 7.55(dd, 1H, J$_{5',6'}$=9.0 Hz, J$_{2',6'}$=2.7 Hz., 6'-H), 7.16(s, 1H, 8-H), 6.97(d, 1H, J$_{5=,6'}$=9.0 Hz, 5'-H), 3.93(s, 3H, —OCH,), 3.91(s, 3H, —OCH$_3$). UV(MeOH)λ$_{max}$(ε): 209.0, 224.0, 249.0, 330.0 nm. IR(KBr)ν$_{max}$: 3448, 2842, 1623, 1506, 1423, 1241 cm$^{-1}$. GC/MS m/z: 341(M$^+$, 100.00), 326(M$^+$-CH$_3$, 98.50), 310(M$^+$-OCH$_3$, 12.5), 295(9.0), 189(13.5), 155(13.8). Anal. (C$_{16}$H$_{14}$ClN$_3$O$_3$.HCl) C, H, N.

4-(2'-Hydroxy-naphthyl-3')-amino-6,7-dimethoxyquinazoline[WHI-P292]

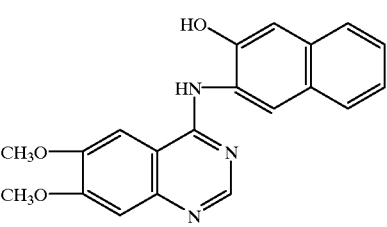

Yield 87.41%; m.p.277.0–279.0° C., IR(KBr)ν$_{max}$: 3479, 3386, 3036, 2901, 1632, 1581, 1504, 1437, 1281 cm$^{-1}$. $^1$H NMR(DMSO-d$_6$): δ11.38(s, 1H, —NH), 10.35(s,, 1H, —OH), 8.73(s, 1H, 2-H), 8.25(s, 1H, 5-H), 7.93–7.30(m,6H, 1', 4', 5', 6', 7', 8'-H), 7.37(s, 1H, 8H), 4.00(s, 6H, —OCH$_3$). GC/MS m/a: 281(41.0), 253(11.0), 207(100.0). Anal. (C$_{20}$H$_{17}$N$_3$O$_3$.HCl) C, H, N.

Cytotoxic Compounds

As shown in the Examples below, a hydroxyl substituent on the phenyl ring (R$_1$–R$_5$) appears to be necessary for cytotoxic effects of the novel substituted compounds of the invention, while a second substitution in this ring, e.g., with a halogen such as bromine (Br), enhances the cytotoxic effect of the compound. In the method of the invention, the cytotoxic effects of these compounds is achieved by contacting brain tumor cells with micromolar amounts of the inhibitory compound. Particularly useful cytotoxic compounds include WHI-P154 (3-Br, 4-OH substituted) and WHI-P131 (4-OH substituted), and WHI-P292 (1-OH napthalene-substituted). More particularly useful are conjugates of these compounds with a targeting moiety such as EGF, having cytotoxic activity at nanomolar concentrations.

As described above, compounds useful in the method of the invention also include those substituted with SH or NH$_2$ in place of the demonstrated hydroxy substitutions.

Compounds for Inhibiting Adhesion/Migration

The Examples below further demonstrate the effectiveness of the hydroxy-substituted quinazoline compounds of the invention as inhibitors of brain tumor cell adhesion to extracellular matrix and of tumor cell migration. Each of the tested compounds having a hydroxy substituents on the phenyl ring demonstrated inhibitory activity against glioblastoma cell adhesion/migration. Particularly potent and useful inhibitory compounds include WHI-P154, WHI-P131, and WHI-P292.

Useful compounds of the invention are tested for the ability to prevent adhesion/migration of brain tumor cells by assays described in the Examples below. Such assays include inhibition of cell binding to extracellular matrix proteins in the presence of the inhibitory compound as compared with a non-inhibitory control; inhibition of brain tumor cell invasion into Matrigel Matrix according to the method published by Albini et.al., 1987, *Cancer Res.* 47:3239; and inhibition of focal adhesion plaques and actin polymerization in the presence of the inhibitory compound as compared with a non-inhibitory control. Conjugation of the inhibitory compounds to a targeting moiety, EGF, enhanced the inhibitory activity of the compound WHI-P154.

In the method of the invention, brain tumor cells are contacted with approximately micromolar concentrations of the inhibitory compounds to inhibit tumor cell adhesion and invasion/migration into non-diseased tissue. This is important, for example, during ablation surgery when cells may be dispersed. Adhesion of cells to ECM coupled with the aggressive malignant nature of brain tumor cells can result in new tumor growth at the adhesion site. Inhibition of adhesion and migration by administering the compounds of the invention thereby inhibits new tumor growth.

Synthesis of Novel Hydroxy-Substituted Quinazoline Derivatives

The hydroxy-substituted quinazoline derivatives of the invention can be synthesized from a key starting material, 4-chloro-6,7-dimethoxyquinazoline, prepared using published procedures (Nomoto, et al., 1990, *Chem. Pharm. Bull.,* 38:1591–1595; Thomas, C. L., 1970, *Academic Press*, New York, N.Y., "I. Synthesis of quinazoline derivatives") as outlined below in Scheme 1 and as described more fully in the Examples below:

Scheme 1

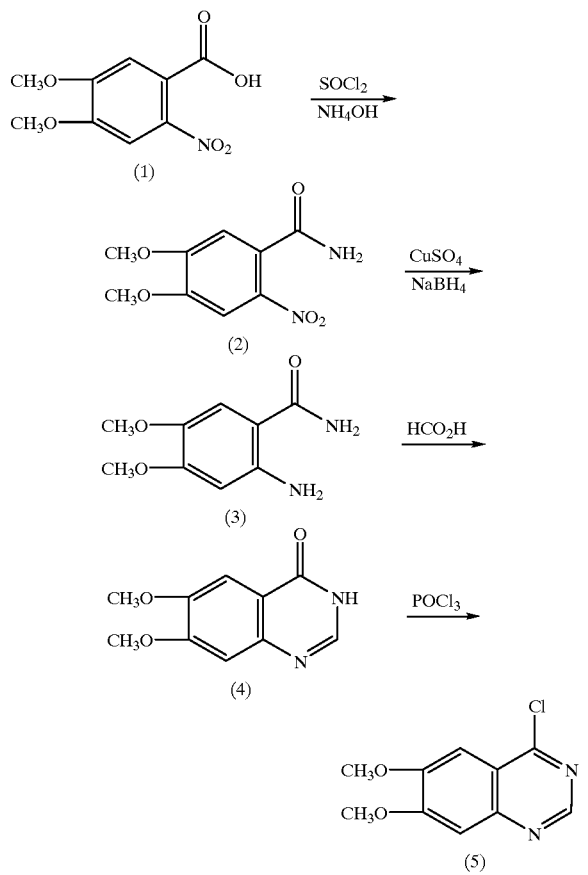

The compounds of the invention are then prepared by the condensation of 4-chloro-6,7-dimethoxyquinazoline with the appropriate substituted aniline as outlined below in Scheme 2:

Scheme 2

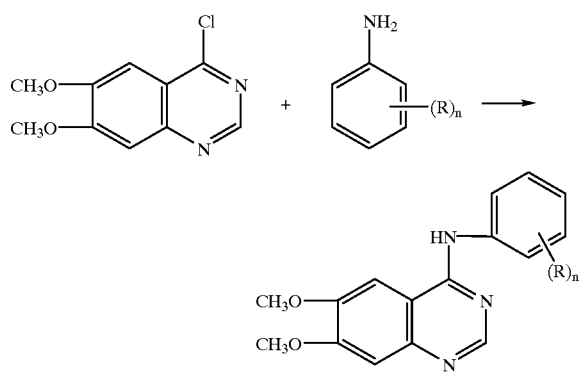

R = substituent; n = number

In a similar manner, compounds of the invention where X is S or O, or where X is alkyl, such as $CH_2$ are synthesized from a precursor compound, reacting the ring moiety with the desired substitution to produce the desired product. These synthetic methods are know to those in the art, and include, for example, those shown in Scheme 3 below.

Scheme 3

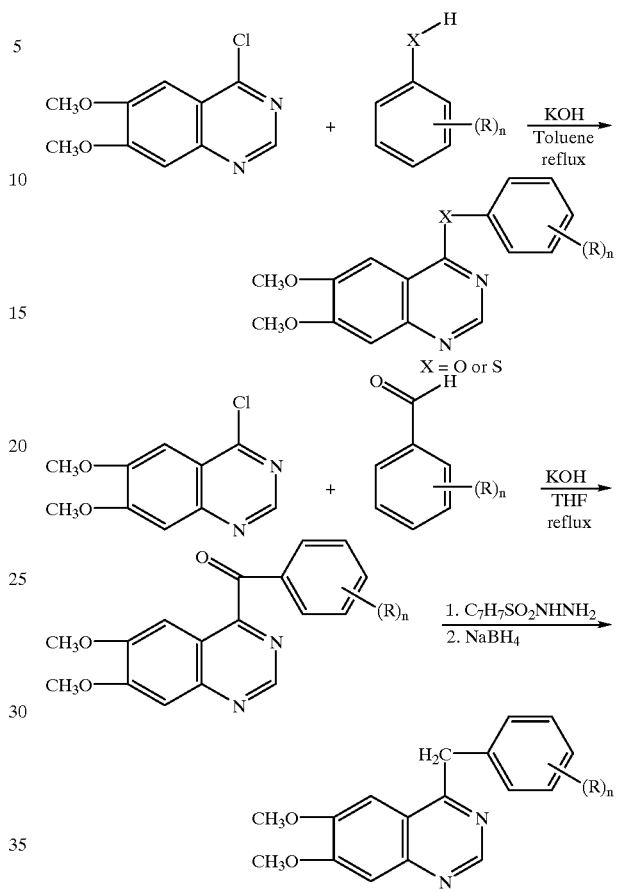

Conjugates of the Invention

The term "conjugate" is meant to include a compound formed as a composite between two or more molecules. More specifically, in the present invention, the novel hydroxy-substitutes quinazoline derivatives are bonded, for example, covalently bonded, to cell-specific targeting moieties forming a conjugate compound for efficient and specific delivery of the agent to a cell of interest.

Targeting Moiety

The phrase "targeting moiety" is meant to include a molecule which serves to deliver the compounds of the invention to a specific site for the desired activity. Targeting moieties include, for example, molecules that specifically bind molecules on a specific cell surface. Such targeting moieties useful in the invention include anti-cell surface antigen antibodies, growth factors which bind to cell surface receptors such as EGF and its receptor EGF-R. Cytokines, including interleukins and factors such as granulocyte/macrophage stimulating factor (GMCSF) are also specific targeting moieties, known to bind to specific cells expressing high levels of their receptors.

Epidermal Growth Factor (EGF) and Its Receptor (EGF-Rc)

Human Epidermal Growth Factor (hEGF) is commercially available in a highly purified form, for example, from Upstate Biotechnology, Inc. (Lake Placid, N.Y.) (Lot No. 01-107C). This protein ligand is known to bind specifically and with high affinity to receptors located on the surface of EGF-responsive cells. Expression of the EFG-Rc is increased in EGF-responsive cells, including hyperplastic neointima cells.

For use in the conjugates of the present invention, recombinant human EGF (hrEGF) is preferred, although it is anticipated that hEGF and hEGF analogs that specifically bind hEGF-Rc on neointima cells will similarly inhibit migration of vascular cells and formation of hyperplastic neointima cell growth when conjugated.

Human epidermal growth factor (EGF) is a 53 amino acid, single-chain, 6216 daltons polypeptide, which exerts biologic effects by binding to a specific 170 kDa cell membrane epidermal growth factor receptor (EGF-receptor/ErbB-1) (Fix, S. B., 1994, *Breast Cancer Research & Treatment*, 29:41–49; Earp et al., 1995, *Breast Cancer Research & Treatment*, 35:115–132; Wright, et al., 1995, *J. Biol. Chem.*, 270:12085–12093; Broome and Hunter, 1996, *J. Biol. Chem*, 271:16798–16806). The human EGF-receptor consists of an extracellular domain with a high cysteine content and N-linked glycosylation, a single transmembrane domain, and a cytoplasmic domain with protein tyrosine kinase (PTK) activity.

Binding of EGF to the EGF-receptor/ErbB-1 results in receptor dimerization with itself or other members of the Erb-B (subtype I) transmembrane PTK family (e.g., Erb-B2, Erb-B3), resulting in activation with autophosphorylation of the PTK domain (Muthuswamy, S. K., 1994, *Molecular & Cellular Biology*, 14:735–743); Ottenhoff-Kalff et al., 1992, *Cancer Research*, 52:4773–4778). The EGF-receptor is physically and functionally associated with Src protooncogene family PTK, including p60$^{STC}$ (Muthuswamy, S. K., 1994, *Molecular & Cellular Biology*, 14:735–743; Ottenhoff-Kalff et al., 1992, *Cancer Research*, 52:4773–4778; Aikyama et al., 1987, *J. Biol. Chem.*, 262:5592–5595). This association is believed to be an integral part of the signaling events mediated by the EGF-receptor (Ottenhoff-Kalff et al., 1992, *Cancer Research*, 52:4773–4778).

Conjugate Formation

To form the conjugates of the invention, targeting moieties are covalently bonded to sites on the hydroxy-substituted quinazoline compounds. The targeting moiety, which is often a polypeptide molecule, is bound to compounds of the invention at reactive sites, including $NH_2$, SH, CHO, COOH, and the like. Specific linking agents are used to link the compounds. Preferred linking agents are chosen according to the reactive site to which the targeting moiety is to be attached.

Methods for selecting an appropriate linking agent and reactive site for attachment of the targeting moiety to the compound of the invention are known, and are described, for example, in Herrnanson, et al., *Bioconjugate Techniques*, Academic Press, 1996; Hermanson, et al., *Immobilized Affinity Ligand Techniques*, Academic Press, 1992; and *Pierce Catalog and Handbook*, 1996, pp. T155–T201. One exemplary method for conjugating EGF is described in the Examples below.

Administration Methods

The conjugates of the present invention can be formulated as pharmaceutical compositions and administered to a mammalian host, including a human patient in a variety of forms adapted to the chosen route of administration and suitable for administration of the small molecule or its conjugate. Preferred administration routes include orally. parenterally, as well as intravenous, intramuscular or subcutaneous routes.

It is preferred that the conjugate of the present invention be administered parenterally, i.e., intravenously or intraperitoneally, by infusion or injection. In one embodiment of the invention, the compounds may be administered directly to a tumor by tumor injection; by injecting the compound into the brain, e.g., into the ventricular fluid; or by systemic delivery by intravenous injection. The compounds of the invention, including the conjugates, are of a size and composition expected to have ready access to the brain across the blood-brain barrier.

Solutions or suspensions of the conjugates can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Tumor Treatment

For purposes of this invention, a method of tumor treatment includes contacting brain tumor cells with a compound of the invention in order to achieve an inhibition of tumor cell growth, a killing of tumor cells, and/or increased patient survival time. Treatment of tumors, by the method of the invention, also includes the prevention of the adhesion and migration of tumor cells, thereby inhibiting metastases.

The cytotoxic and adhesion/migration-inhibiting compounds of the invention are suitable for use in mammals. As used herein, "mammals" means any class of higher vertebrates that nourish their young with milk secreted by mammary glands, including, for example, humans, rabbits, and monkeys.

Apoptosis

Apoptosis, or programmed cellular death, is an active process requiring new protein synthesis. Typically, the process requires ATP, involves new RNA and protein synthesis, and culminates in the activation of endogenous endonucleases that degrade the DNA of the cell, thereby destroying the genetic template required for cellular homostasis. Apoptosis is observed in controlled deletion of cells during metamorphosis, differentiation, and general cell turnover and appears normally to be regulated by receptor-coupled events. For these reasons, apoptosis has been called "programmed cell death" or "cell suicide." While every cell likely has the genetic program to commit suicide, it is usually suppressed. Under normal circumstances, only those cells no longer required by the organism activate this self-destruction program.

Apoptotic cell death is characterized by plasma membrane blebbing, cell volume loss, nuclear condensation, and endonucleolytic degradation of DNA at nucleosome intervals. Loss of plasma membrane integrity is a relatively late event in apoptosis, unlike the form of cell death termed necrosis, which can be caused by hypoxia and exposure to certain toxins and which is typically characterized early-on by increased membrane permeability and cell rupture.

Adhesion/Migration

Adhesion is meant to include that activity of a cell, such as a tumor cell, by which it adheres to extracellular matrix proteins, including laminin, fibronectin, and collagen. Adhesion assays are known, and include, for purposes of this invention, the adherence of tumor cells to plates coated with extracellular matrix proteins.

Migration is meant to include that activity of tumor cells by which they migrate through extracellular matrix and invade tissues. Assays for migration include the ability of cells to migrate through a matrix formed of extracellular matrix, such as MATRIGEL matrix, as well as evaluation of the cell's cytoskeletal organization including actin cytoskeletal rearrangement and changes in focal adhesions as described in the following Examples.

Useful Dose

When used in vivo to selectively kill brain tumor cells or to inhibit brain tumor cell adhesion/migration, the administered dose is that effective to have the desired effect, e.g., sufficient to reduce or eliminate brain tumors, or sufficient to inhibit adherence/migration of tumor cells. Appropriate amounts can be determined by those skilled in the art, extrapolating using known methods and relationships, from the in vitro and in vivo data provided in the Examples. Based on the SCID mouse pharmacology data contained in this application, effective exposure levels are expected to be achieved.

In general, the dose of the novel substituted quinozalines effective to achieve brain tumor cell apoptosis, reduction in tumors, and increased survival time, is that which administers micromolar amounts of the compound to the cells, preferably 100 micromolar or greater. The required dose is lessened by conjugation of the compound to a targeting moiety, for example, to preferably 100 nanomolar or greater concentrations.

For cell adhesion and migration inhibitory activities, the compound is administered generally at lower dosages, in the range of 100 micromolar or less.

The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-tumor therapies. In such combination therapy, the administered dose of the hydroxy-substituted quinazoline derivatives would be less than for single drug therapy.

EXAMPLES

The invention may be further clarified by reference to the following Examples, which serve to exemplify some of the preferred embodiments, and not to limit the invention in any way.

Example 1
Synthesis of Quinazoline Derivatives

All chemicals were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under a nitrogen atmosphere.

The key starting material, 4-chloro-6,7-dimethoxyquinazoline, was prepared using published procedures (Nomoto, et al., 1990, *Chem. Pharm. Bull.*, 38:1591–1595; Thomas, C. L., 1970, *Academic Press*, New York, N.Y., "I. Synthesis of quinazoline derivatives") as outlined below in Scheme 1:

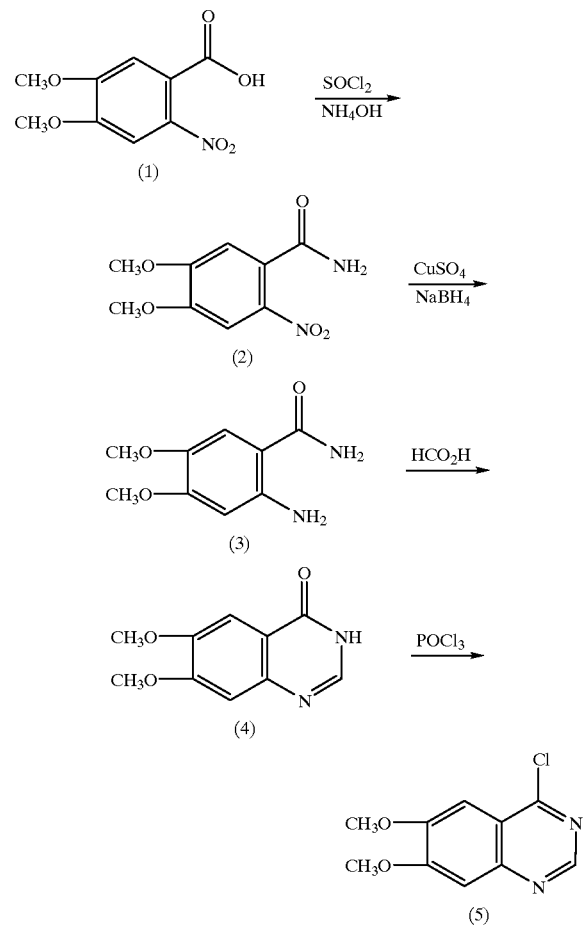

Specifically, 4,5-dimethoxy-2-nitrobenzoic acid (compound 1) was treated with thionyl chloride to form acid chloride, followed by reacting with ammonia to yield 4,5-dimethoxy-2-nitrobenzamide (compound 2). Compound 2 was reduced with sodium borohydride in the presence of catalytic amounts of copper sulphate to give 4,5-dimethoxy-2-aminobenzamide (compound 3), which was directly refluxed with formic acid to yield 6,7-dimethoxyquinazoline-4(3H)-one (compound 4). Compound 4 was refluxed with phosphorus oxytrichloride to give 4-chloro-6,7-dimethoxyquinazoline (compound 5) in good yield.

Substituted quinazoline derivatives were prepared by the condensation of 4-chloro-6,7-dimethoxyquinazoline with substituted anilines as outlined below in Scheme 2:

Scheme 2

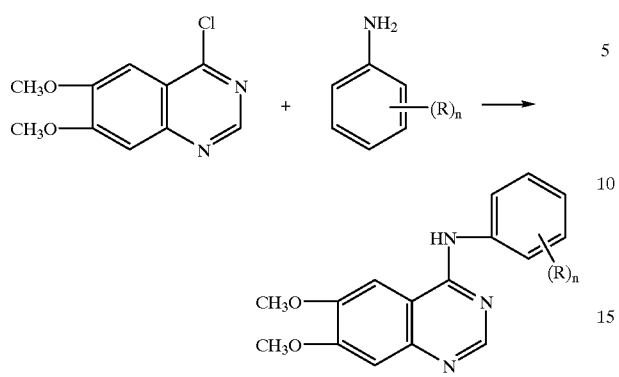

R = substituent; n = number

Specifically, a mixture of 4-chloro-6,7-dimethoxyquinazoline (448 mg, 2 mmols) and the substituted aniline (2.5 mmols) in EtOH (20 ml) was heated to reflux. After refluxing for 4–24 hours, an excess amount of $Et_3N$ was added, and the solvent was concentrated to give the crude product which was recrystalized from DMF.

As discussed above, the novel hydroxy-substituted quinazoline derivatives of the invention were created by reacting substituted anilines with the key starting material, 4-chloro-6,7-dimethoxyquinazoline. Each of the anilines to synthesize the compounds is shown in the table below.

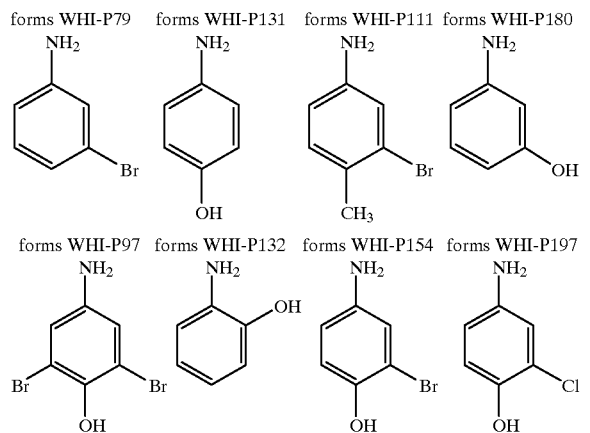

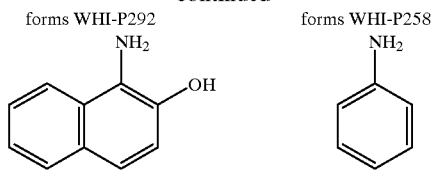

Example 2

Characterization of Substituted Quinazoline Derivatives

The substituted quinazoline derivatives were synthesized as described in Example 1 and characterized. Each structure is shown below, along with its identifying analytical test results. Proton and carbon Nuclear Magnetic Resonance ($^1H$ and $^{13}C$ NMR) spectra were recorded on a Mercury 2000 Varian spectrometer operating at 300 MHz and 75 MHz, respectively, using an automatic broad band probe. Unless otherwise noted, all NMR spectra were recorded in $CDCl_3$ at room temperature. $^1H$ chemical shifts are quoted in parts per million (δ in ppm) downfield from tetramethyl silane (TMS), which was used as an internal standard at 0 ppm and s, d, t, q, m designate singlet, doublet, triplet, quartet and multiplet, respectively. Melting points were determined using a Fisher-Johns melting apparatus and are uncorrected. UV spectra were recorded using a Beckmann Model #DU 7400 UV/V is spectrometer with a cell path length of 1 cm. Methanol was used as the solvent for the UV spectra. Fourier Transform Infrared spectra were recorded using an FT-Nicolet model Protege #460 instrument. The infrared spectra of the liquid samples were run as neat liquids using KBr discs. The KBr pellet method was used for all solid samples. The GC/mass spectrum analysis was conducted using a Hewlett-Packard GC/mass spectrometer model #6890 equipped with a mass ion detector and Chem Station software. The temperature of the oven was steadily increased from 70° C. to 250° C. and the carrier gas was helium.

---

4-(3'-Bromophenyl)-amino-6,7-dimethoxyquinazoline [WHI-P79]

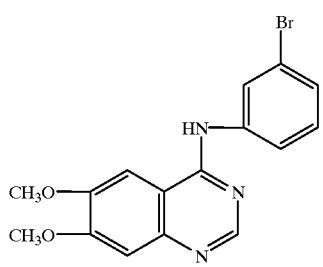

yield 84.17%; m.p. 246.0–249.0° C. UV(MeOH)$\lambda_{max}$: 217.0, 227.0, 252.0 nm; IR(KBr)$\upsilon_{max}$: 3409, 2836, 1632, 1512, 1443, 1243, 1068 $cm^{-1}$; $^1H$ NMR(DMSO-$d_6$): δ 10.42(br, s, 1H, NH), 8.68(s, 1H, 2-H), 8.07–7.36(m, 5H,5,2'4'5'6'-H), 7.24(s, 1H, 8H), 3.98(s, 3H, —$OCH_3$), 3.73(s, 3H, —$OCH_3$); GC/MS m/z 361 ($M^+$ + 1, 61.83), 360($M^+$, 100), 359($M^+$ − 1, 63.52), 344(11.34), 222(10.87), 140(13.65). Anal. ($C_{16}H_{14}BrN_3O_2$) C, H, N.

-continued 4-(3',5'-Dibromo-4'-hydroxylphenyl)-amino-6,7-dimethoxyquinazoline [WHI-P97]

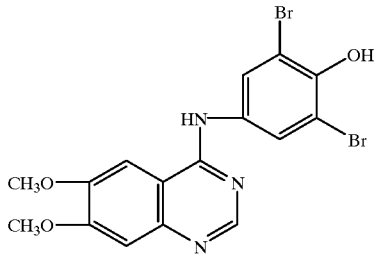

yield 72.80%; m.p. >300.0° C. UV(MeOH)$\lambda_{max}$: 208.0, 210.0, 245.0, 320.0 nm; IR(KBr)$\upsilon_{max}$: 3504(br), 3419, 2868, 1627, 1512, 1425, 1250, 1155 cm$^{-1}$; $^1$H NMR(DMSO-d$_6$): δ 9.71(s, 1H, —NH), 9.39(s, 1H, —OH), 8.48(s, 1H, 2-H), 8.07(s, 2H, 2',6'-H), 7.76(s, 1H,5-H), 7.17(s, 1H, 8-H), 3.94(s, 3H, —OCH$_3$), 3.91(s, 3H, —OCH$_3$). GC/MS m/z 456(M$^+$ + 1, 54.40), 455(M$^+$, 100.00), 454(M$^+$ − 1, 78.01), 439(M$^+$ —OH, 7.96), 376(M$^+$ + 1 —Br, 9.76), 375(M$^+$ —Br, 10.91), 360(5.23). Anal. (C$_{16}$H$_{13}$Br$_2$N$_3$O$_3$) C, H, N.

4-(3'-Bromo-4'-methylphenyl)-amino-6,7-dimethoxyquinazoline [WHI-P111]

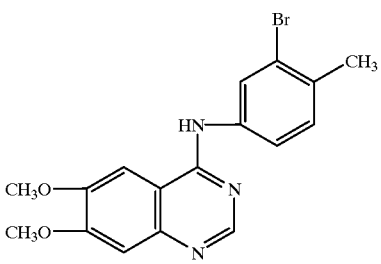

yield 82.22%; m.p. 225.0–228° C. $^1$H NMR(DMSO-d$_6$): δ 10.23(s, 1H, —NH), 8.62(s, 1H, 2-H), 8.06(D, 1h, j$_{2',6'}$=2.1 Hz. 2'-H), 7.89(s, 1H, 5-H), 7.71(dd, 1H, J$_{5',6'}$=8.7 Hz, J$_{2',6'}$=2.1 Hz, 6'-H), 7.37(d, 1H, J$_{5',6'}$=8.7 Hz, 5'-H, 7.21(s, 1H, 8-H), 3.96(s, 3H, —OCH$_3$), 3.93(s, —OCH$_3$). UV (MeOH)$\lambda_{max}$(ε): 204.0, 228.0, 255.0, 320.0 nm. IR(KBr)$\upsilon_{max}$: 3431, 3248, 2835, 1633, 1517, 1441, 1281, 1155 cm$^{-1}$. GC/MS m/z 375(M$^+$ + 1, 76.76), 374(M$^+$, 100.00), 373(M$^+$ − 1, 76.91), 358(M$^+$ + 1 —OH, 11.15), 357(1.42), 356(6.31). Anal. (C$_{17}$H$_{16}$BrN$_3$O$_2$HCl) C, H, N.

4-(4'-Hydroxylphenyl)-amino-6,7-dimethoxyquinazoline [WHI-P131]

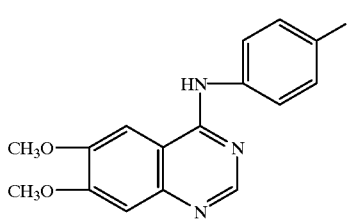

yield 84.29%; m.p. 245.0–248.0° C. UV(MeOH)$\lambda_{max}$: 203.0, 222.0, 251.0, 320.0 nm; IR(KBr)$\upsilon_{max}$: 3428, 2836, 1635, 1516, 1443, 1234 cm$^{-1}$; $^1$H NMR(DMSO-d$_6$): δ 11.21(s, 1H, —NH), 9.70(s, 1H, —OH), 8.74(s, 1H, 2-H), 8.22(s, 1H, 5-H), 7.40(d, 2H, J=8.9 Hz, 2',6'-H), 7.29(s, 1H, 8-H), 6.85(d, 2H, J=8.9 Hz, 3',5'-H), 3.98(s, 3H, —OCH$_3$), 3.97(s, 3H, —OCH$_3$). GC/MS m/z 298 (M$^+$ + 1, 100.00), 297 (M$^+$, 26.56), 296(M$^+$ − 1, 12.46). Anal. (C$_{16}$H$_{15}$N$_3$O$_3$HCl) C, H, N.

4-(2'-Hydroxyphenyl)-amino-6,7-dimethoxyquinazoline [WHI-P132]

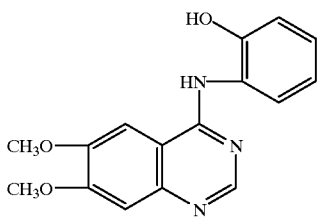

yield 82.49%; m.p. 255.0–258.0° C. $^1$H NMR(DMSO-d$_6$): δ 9.78(s, 1H, —NH), 9.29(s, 1H, —OH), 8.33(s, 1H, 2-H), 7.85(S, 1H, 5-H), 7.41–6.83(m, 4H, 3',4',5',6'-H), 7.16(s, 1H, 8-H), 3.93(s, 3H, —OCH$_3$), 3.92(s, 3H, —OCH$_3$). UV(mEoh)$\lambda_{max}$(ε): 203.0, 224.0, 245.0, 335.0 nm. IR(KBr)$\upsilon_{max}$: 3500 (br), 3425, 2833, 1625, 1512, 1456, 1251, 1068 cm$^{-1}$. GC/MS m/z 298(M$^+$ + 1, 8.91), 297(M$^+$, 56.64), 281(M$^+$ + 1 —OH, 23.47), 280(M$^+$ —OH, 100.00). Anal. (C$_{16}$H$_{15}$N$_3$O$_3$HCl) C, H, N.

4-(3'-Bromo-4'-hydroxylphenyl)-amino-6,7-dimethoxyquinazoline [WHI-P154)

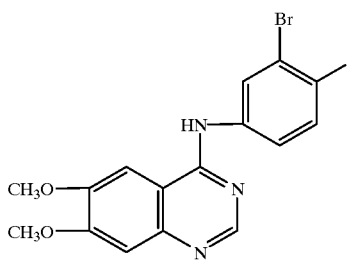

yield 89.90%; m.p. 233.0–233.5° C. UV(MeOH)$\lambda_{max}$: 203.0, 222.0, 250.0, 335.0 nm; IR(KBr)$\upsilon_{max}$: 3431 br, 2841, 2624, 1498, 1423, 1244 cm$^{-1}$; $^1$H NMR(DMSO-d$_6$): δ 10.08(s, 1H, —NH), 9.38(s, 1H, —OH), 8.40(s, 1H, 2-H), 7.89(d, 1H, J$_{2',5'}$=2.7Hz, 2'-H), 7.75(s, 1H, 5-H), 7.55(dd, 1H, J$_{5',6'}$=9.0 Hz, J$_{2',6'}$= 2.7 Hz, , 6'-H), 7.14(s, 1H, 8-H), 6.97(d, 1H, J$_{5',6'}$= 9.0 Hz, 5'-H), 3.92(s, 3H, —OCH$_3$), 3.90(s, 3H, —OCH$_3$). GC/MS m/z 378 (M$^+$ + 2, 90.68), 377(M$^+$ + 1, 37.49), 376(M$^+$, 100.00), 360(M$^+$, 3.63), 298(18.86), 282(6.65). Anal. (C$_{16}$H$_{14}$N$_3$O$_3$HCl) C, H, N.

-continued 4-(3'-Hydroxylphenyl)-amino-6,7-dimethoxyquinazoline [WHI-P180]

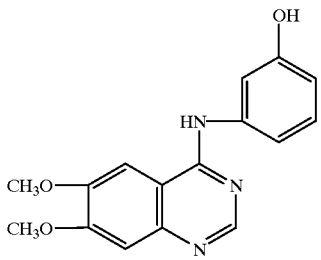

yield 71.55%; m.p. 256.0–258.0° C. $^1$HNMR(DMSO-d$_6$); δ 9.41(s, 1H, —NH), 9.36(s, 1H, —OH), 8.46(s, 1H, 2-H), 7.84(s, 1H, 5-H), 7.84–6.50(m, 4H, 2',4',5',6'-H), 7.20(s, 1H, 8-H), 3.96(S, 1H, —OCH$_3$), 3.93(s, 3H, —OCH$_3$). UV(MeOH)λ$_{max}$(ε): 204.0, 224.0, 252.0, 335.0 nm. IR(KBr)υ$_{max}$: 3394, 2836, 1626, 1508, 1429, 1251 cm$^1$. GM/MS m/z: 297(M$^+$, 61.89), 296(M$^+$, 61.89), 296(M$^+$– 1, 100.00), 280(M$^+$ —OH, 13.63), Anal. (C$_{16}$H$_{15}$N$_3$O$_3$.HCl) C, H, N.

4-(3'-Chloro-4'-Hydroxylphenyl)-amino-6,7-dimethoxyquinazoline [WHI-P197]

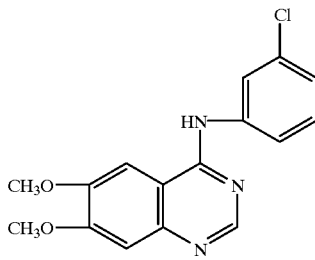

yield 84.14%; m.p. 245.0° C. (dec). $^1$H NMR(DMSO-d$_6$): δ 10.00(s, 1H, —NH), 9.37(s, 1H, —OH), 8.41(s, 1H, 2-H), 7.78(s, 1H, 5-H), 7.49(d, 1H, J$_{2',6}$=2.7 Hz, 2'-H), 7.55(dd, 1H, J$_{5',6'}$=9.0 Hz, J$_{2',6}$=2.7 Hz., 6'-H), 7.16(s, 1H, 8-H), 6.97(d, 1H, J$_{5',6}$=9.0 Hz, 5'-H), 3.93(s, 3H, —OCH$_3$,), 3.91(s, 3H, —OCH$_3$). UV(MeOH)λ$_{max}$(ε): 209.0, 224.0, 249.0, 330.0 nm. IR(KBr)υ$_{max}$: 3448, 2842, 1623, 1506, 1423, 1241 cm$^{-1}$. GC/MS m/z: 341(M$^+$, 100.00), 326(M$^+$ —CH$_3$, 98.50), 310(M$^+$ —OCH$_3$, 12.5), 295(9.0), 189(13.5), 155(13.8). Anal. (C$_{16}$H$_{14}$ClN$_3$O$_3$.HCl) C, H, N.

4-(phenyl)-amino-6,7-dimethoxyquinazoline [WHI-P258]

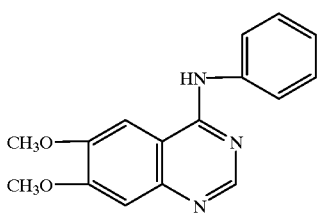

yield 88.6%; m.p. 258.0–260.0° C. $^1$HNMR(DMSO-d$_6$): δ 11.41(s, 1H, —NH), 8.82(s, 1H, 2-H), 8.32(s, 1H, 5-H), 7.70–7.33(m, 5H, 2',3',4',5',6'-H), 7.36(s, 1H, 8H), 4.02(s, 3H, —OCH$_3$), 4.00(s, 3H, —OCH$_3$), 4.00(s, 3H, —OCH$_3$). UV(MeOH)λ$_{max}$(ε): 210.0, 234.0, 330.0 nm. IR(KBr)υ$_{max}$: 2852, 1627, 1509, 1434, 1248 cmhu –1. GC/MS m/z 282(M$^+$ + 1, 10.50), 281(M$^+$, 55.00), 280(M$^+$ – 1, 100.00), 264(16.00), 207(8.50). Anal. (C$_{16}$H$_{15}$N$_3$O$_2$) C, H, N.

4-(2'-Hydroxy-naphthyl-3'-amino-6,7-dimethoxyquinazoline [WHI-P292].

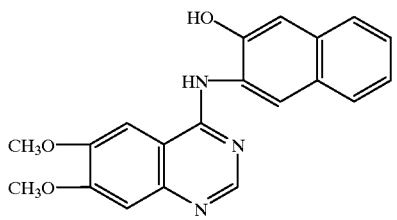

Yield 87.41%; m.p. 277.0–279.0° C., IR(KBr)υ$_{max}$: 3479, 3386, 3036, 2901, 1632, 1581, 1504, 1437, 1281 cm$^{-1}$. $^1$H NMR(DMSO-d$_6$): δ 11.38(s, 1H, —NH), 10.35(s,, 1H, —OH), 8.73(s, 1H, 2-H), 8.25(s, 1H, 5-H), 7.93–7.30(m, 6H, 1',4', 5',6',7',8'-H), 7.37(s, 1H, 8H), 4.00(s, 6H, —OCH$_3$). GC/MS m/a: 281(41.0), 253(11.0), 207(100.0). Anal. (C$_{20}$H$_{17}$N$_3$O$_3$.HCl) C, H, N.

Example 3
Cytotoxicity of Substituted Quinazoline Derivatives

The cytotoxicity of the substituted quinazoline derivative compounds against human glioblastoma cells was evaluated. The relative importance of particular substituent group on the compounds was also studied. The substituted quinazoline derivative compounds, prepared as described above for Example 1, were tested, along with DMSO and Genistein as controls.

Cytotoxicity Assay

The cytotoxicity assay of various compounds against human brain tumor cell lines was performed using the MTT (3-[4,5-dimethylthiazol-2-yl]-2,5-diphenyl tetrazolium bromide) assay (Boehringer Mannheim Corp., Indianapolis, Ind.). Briefly, exponentially growing brain tumor cells were seeded into a 96-well plate at a density of 2.5×10$^4$ cells/well and incubated for 36 hours at 37° C. prior to drug exposure. On the day of treatment, culture medium was carefully aspirated from the wells and replaced with fresh medium containing the quinazoline compounds WHI-P79, WHI-P97, WHI-P111, WHI-P131, WHI-P132, WHI-P154, WHI-P180, WHI-P197, WHI-P258, unconjugated EGF, or EGF-P154, as well as the tyrosine kinase inhibitory isoflavone genistein (GEN) at concentrations ranging from 0.1 to 250 μM. Triplicate wells were used for each treatment.

Human glioblastoma cell line U373 was obtained from American Type Culture Collection (Rockville, Md.) and maintained as a continuous cell line in Dulbecco's modified Eagles's medium supplemented with 10% fetal bovine serum and antibiotics. The B-lineage acute lymphoblastic leukemia cell line Nalm-6 was used as a negative control.

The cells were incubated with the various compounds for 24–36 hours at 37° C. in a humidified 5% CO$_2$ atmosphere. To each well, 10 μl of MTT (0.5 mg/ml final concentration)

was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 nm. To translate the $OD_{540}$ values into the number of live cells in each well, the $OD_{540}$ values were compared to those on standard $OD_{540}$—versus—cell number curves generated for each cell line. The percent survival was calculated using the formula:

$$\% \text{ Survival} = \frac{\text{live cell number [test]}}{\text{live cell number [control]}} 100$$

The IC50 values were calculated by non-linear regression analysis.

In situ Detection of Apoptosis

The demonstration of apoptosis was performed by the in situ nick-end-labeling method using ApopTag in situ detection kit (Oncor, Gaithersburg, Md.) according to the manufacturer's recommendations. Exponentially growing cells were seeded in 6-well tissue culture plates at a density of $50\times10^4$ cells/well and cultured for 36 hours at 37° C. in a humidified 5% $CO_2$ atmosphere. The supernatant culture medium was carefully aspirated and replaced with fresh medium containing unconjugated EGF or EGF-P154 at a concentration of 10, 25 or 50 μg/ml. After a 36 hour incubation at 37° C. in a humidified 5% $CO_2$ incubator, the supernatants were carefully aspirated and the cells were treated for 1–2 minutes with 0. 1% trypsin. The detached cells were collected into a 15 ml centrifuge tube, washed with medium and pelleted by centrifugation at 1000 rpm for 5 minutes. Cells were resuspended in 50 μl of PBS, transferred to poly-L-lysine coated coverslips and allowed to attach for 15 minutes. The cells were washed once with PBS and incubated with equilibration buffer for 10 minutes at room temperature.

After removal of the equilibration buffer, cells were incubated for 1 hour at 37° C. with the reaction mixture containing terminal deoxynucleotidyl transferase (TdT) and digoxigenin-11-UTP for labeling of exposed 3'-hydroxyl ends of fragmented nuclear DNA. The cells were washed with PBS and incubated with anti-digoxigenin antibody conjugated to FITC for 1 hour at room temperature to detect the incorporated dUTP. After washing the cells with PBS, the coverslips were mounted onto slides with Vectashield containing propidium iodide (Vector Labs, Burlingame. Calif.) and viewed with a confocal laser scanning microscope. Non-apoptotic cells do not incorporate significant amounts of dUTP due to lack of exposed 3-hydroxyl ends, and consequently have much less fluorescence than apoptotic cells which have an abundance of exposed 3'-hydroxyl ends. In control reactions, the TdT enzyme was omitted from the reaction mixture.

Results

The identity of the specific substituents on each aniline moiety are summarized below:

| Quinazoline Derivatives | Identity of Substituents |
|---|---|
| WHI-P79 | 3-Br |
| WHI-P97 | 3-Br, 5-Br, 4-OH |
| WHI-P111 | 3-Br, 4-$CH_3$ |
| WHI-P131 | 4-OH |
| WHI-P132 | 2-OH |
| WHI-P154 | 3-Br, 4-OH |
| WHI-P180 | 3-OH |
| WHI-P197 | 3-Cl, 4-OH |
| WHI-258 | H |
| WHI-292 | 1-OH Naphthyl |

The results of the cytotoxicity assay against brain tumor cells are shown in FIGS. 1A and 1B. In summary, those compounds having hydroxy substitutions on the phenyl ring, were effective in killing brain tumor cells. The unsubstituted compound P258 and the 3-Br-substituted potent TK inhibitor P79 were ineffective in killing brain tumor cells. Genistein and DMSO controls were also ineffective.

Those substituted quinazoline derivatives having an hydroxyl group on the aniline moiety demonstrated cytotoxic activity. Four compounds tested possessed a single hydroxyl group; at position 4 (WHI-P131), at position 2 (WHI-P132), at position 3 (WHI-P180), and at position 1 (WHI-P292). All four exhibited significant cytotoxicity, with the WHI-P180 (3-OH) compound demonstrating slightly stronger effects than the other two.

Compounds were having both a hydroxyl substituent and a halogen substituents were also potent cytotoxic agents. The structure of WHI-P197 (3-Cl, 4-OH) differs from that of WHI-P131 (4-OH) only in the chlorine atom at position 3. As shown in FIGS. 1A and 1B, addition of the chlorine atom did not effect the cytotoxicity of this compound.

The structure of WHI-P154 (3-Br, 4-OH) differs from WHI-P131 (4-OH), only in the bromine atom at position 3. As shown in FIGS. 1A and 1B, the addition of the bromine atom to this compound significantly increased the cytotoxicity of the compound.

The structure of WHI-P97 differs from that of WHI-P154 only in the additional bromine atom added at position 5. FIG. 1 shows that there is essentially no benefit from the added second bromine atom.

WHI-P154, 4-(3'-Bromo-4'-hydroxylphenyl)-amino-6,7-dimethoxyquinazoline exhibited significant cytotoxicity against the U373 human glioblastoma cell line in 3 of 3 independent experiments with a mean (±SE) IC50 value of 167.4±26.9 μM and a composite survival curve IC50 value of 158.5 μM. In contrast, WHI-P79, a potent inhibitor of EGF-R and Src family tyrosine kinases (Bos, et al., 1997, Clin. Cancer Res. 3:2099–2106; Fry, et al., 1994, Science (Washington, D.C.) 265:1093–1095) failed to cause any detectable cytotoxicity to U373 glioblastoma cells. Thus, the cytotoxicity of WHI-P154 to U373 cells cannot be explained by its tyrosine kinase inhibitory properties. This notion was further supported by the inability of the PTK inhibitor genistein (included as controls) to cause detectable cytotoxicity to U373 cells (IC50 value >250 µM; FIG. 1A).

Example 4

Enhanced Cytotoxicity of Conjugated WHI-P154 against Human Glioblastoma Cells

In contrast to normal glial cells and neurons, significant numbers of glioblastoma cells express the EGF receptor (EGF-R) at high levels. Therefore, the EGF-R is a potential target for delivering cytotoxic agents to glioblastoma cells with greater efficiency (Mendelsohn, J. and Baselga, J., 1995, *Biologic Therapy of Cancer: Principles and Practice*, pp. 607–23).

Expression of EGF-R by Glioblastoma Cells

Surface expression of the EGF-R on the U373 and U87 human glioblastoma cell lines (obtained and maintained as described for Example 3) was confirmed with immunofluorescence and confocal laser scanning microscopy using monoclonal antibodies to the extracellular domain of the EGF-R.

Immunofluorescence staining with anti-a-tubulin antibody and the nuclear dye Toto-3 was used in combination with confocal laser scanning microscopy to examine the morphological features of U373 glioma cells treated with either unconjugated EGF or EGF-P154. Cells were fixed in paraformaldehyde, immunostained with monoclonal antibody to EGF-R (green fluorescence) and counterstained with TOTO-3 (blue fluorescence) The immunostained cells were analyzed with a laser scanning confocal microscope. Blue fluorescence represents nuclei. Both cell lines showed a diffuse granular immunoreactivity with the anti-EGF-R antibody (see FIGS. 2A and 2B).

Preparation of EGF-P154 Conjugate

In an attempt to enhance the demonstrated anti-tumor activity of 4-(3'-Bromo-4'-hydroxylphenyl)-amino-6,7-dimethoxyquinazoline (WHI-P154) against glioblastoma cells, by improving its targeting to and cellular uptake by glioblastoma cells, the compound was conjugated to recombinant human EGF, as described below.

Recombinant human EGF (rhEGF) was produced in *E. coli* harboring a genetically engineered plasmid that contains a synthetic gene for human EGF fused at the N-terminus to a hexapeptide leader sequence for optimal protein expression and folding. The rhEGF fusion protein precipitated in the form of inclusion bodies and the mature protein was recovered by trypsin-cleavage followed by purification using ion exchange chromatography and HPLC. The recovered rhEGF was 99% pure by reverse-phase HPLC and SDS-PAGE with an isoelectric point of 4.6±0.2. The endotoxin level was 0.172 EU/mg.

The recently published photochemical conjugation method using the hetero-bifunctional photoreactive crosslinking agent, Sulfosuccinimidyl 6-[4'azido-2'-nitrophenylamino] hexanoate (Sulfo-SANPAH) (Pierce Chemical Co., Rockford, Ill.) was employed for the synthesis of the EGF-P154 conjugate, as described in Uckun, et al., 1995, *Science*, 267:886–891. Sulfo-SANPAH modified rhEGF was mixed with a 10:1 molar ratio of WHI-P154 [50 mM solution in dimethyl sulfoxide (DMSO)] and then irradiated with gentle mixing for 10 minutes with UV light at wavelengths 254–366 nm with a multiband UV light-emitter (Model UVGL-15 Mineralight; UVP, San Gabriel, Calif.). Photolytic generation of a reactive singlet nitrene on the other terminus of EGF-SANPAH in the presence of a 10-fold molar excess of WHI-P154 resulted in the attachment of WHI-P154 to EGF.

Excess WHI-P154 in the reaction mixture was removed by passage through a pre-packed PD-10 column, and 12 kDa EGF-EGF homoconjugates with or without conjugated WHI-P154 as well as higher molecular weight reaction products were removed by size-exclusion high-performance liquid chromatography (HPLC). Reverse phase HPLC using a Hewlett-Packard (HP) 1100 series HPLC instrument was used for separation of EGF-P154 from EGF-SANPAH. After the final purification, analytical HPLC was performed using a Spherisorb ODS-2 reverse phase column (250×4 mm, Hewlett-Packard, Cat.#79992402-584). Prior to the HPLC runs, a Beckman DU 7400 spectrophotometer was used to generate a UV spectrum for each of the samples to ascertain the λmax for EGF-P154, EGF-SANPAH, and unmodified EGF.

Each HPLC chromatogram was subsequently run at wavelengths of 214, 265, and 480 nm using the multiple wavelength detector option supplied with the instrument to ensure optimal detection of the individual peaks in the chromatogram. Analysis was achieved using a gradient flow consisting of 0% to 100% eluent in a time interval of 0to 30 minutes. Five µL samples applied to the above column were run using the following gradient program: 0–5 minutes: 0–20% eluent; 5–20 minutes: 20–100% eluent; 25–30 minutes: 100% eluent; and 30–35 minutes: 100–0% eluent. The eluent was a mixture of 80% acetonitrile (CH3CN), 20% $H_2O$ and 0.1% TFA. Electrospray ionization mass spectrometry (Feng, et al., 1991, *J. Am. Soc. Mass Spectrometry* 2:387–401; Covey, et al., 1988, *Rapid Communications in Mass Spectrometry* 2:249–256) was performed using a PE SCIEX API triple quadruple mass spectrometer (Norwalk. Conn.) to determine the stoichiometry of P154 and EGF in EGF-P154.

Uptake and Internalization of EGF-P154

The kinetics of uptake and cytotoxicity of the EGF-P154 conjugate in U373 glioblastoma cells were analyzed using immunofluorescence and confocal laser microscopy for following the internalized EGF-R and EGF-P154 molecules, as well as morphologic changes in treated cells.

Immunofluorescence was used to (i) examine the surface expression of EGF-receptor (EGF-R) on brain tumor cells, (ii) evaluate the uptake of EGF-P154 by brain tumor cells and (iii) examine the morphologic features of EGF-P154 treated brain tumor cells. For analysis of EGF-R expression and cellular uptake of EGF-P154, U87 and U373 glioblastoma cells were plated on poly-L-lysine coated glass-bottom 35 mm Petri dishes (Mattek Corp., Ashland, Mass.) and maintained for 48 hours. In uptake studies, the culture medium was replaced with fresh medium containing 5 µg/ml EGF, EGF-P154 or unconjugated WHI-P154 and cells were incubated at 37° C. for 5 minutes, 10 minutes, 15 minutes, 30 minutes, 60 minutes, and 24 hours.

At the end of the incubation, cells were washed twice with PBS and fixed in 2% paraformaldehyde. The cells were permeabilized and non-specific binding sites were blocked with 2.5% BSA in PBS containing 0.1% Triton X-100 for 30 minutes. To detect the EGF-R/EGF-P154 complexes, cells were incubated with a mixture of a monoclonal antibody (1:10 dilution in PBS containing BSA and Triton X-100) directed to the extracellular domain of the human EGF-R (Santa Cruz Biotechnologies Inc. Santa Cruz, Calif.) and a polyclonal rabbit anti-P154 antibody (1:500 dilution) for 1 hour at room temperature. After rinsing with PBS, cells were incubated for 1 hour Keith a mixture of a goat anti-mouse IgG antibody conjugated to FITC (Amersham Corp., Arlington Heights, Ill.) and donkey anti-rabbit IgG conjugated to Texas Red (Amersham Corp.) at a dilution of 1:40 in PBS.

Similarly, tubulin expression was examined by immunofluorescence using a monoclonal antibody against α-tubulin (Sigma Chemical Co, St. Louis, Mo.) at a dilution of 1:1000 and an anti-mouse IgG conjugated to FITC. Cells were washed in PBS and counterstained with toto-3 (Molecular Probes Inc., Eugene, Oreg.) for 10 minutes at a dilution of 1:1000. Cells were washed again with PBS and the coverslips were mounted with Vectashield (Vector Labs, Burlingame, Calif.) and viewed with a confocal microscope (Bio-Rad MRC 1024) mounted in a Nikon Labhophot upright microscope.

Cytotoxic Activity

To determine if the improved delivery of WHI-P154 to glioblastoma cells by conjugation to EGF resulted in potentiation of its anti-tumor activity, the cytotoxic activities of EGF-P154 and unconjugated WHI-P154 against U373 and U87 human glioblastoma cell lines were analyzed in dose response studies using in vitro MTT assays, as described above for Example 3. Apoptosis was also evaluated using the nick-end-labeling assay, as described for Example 3. The data are discussed below.

Results

Figure 2B:
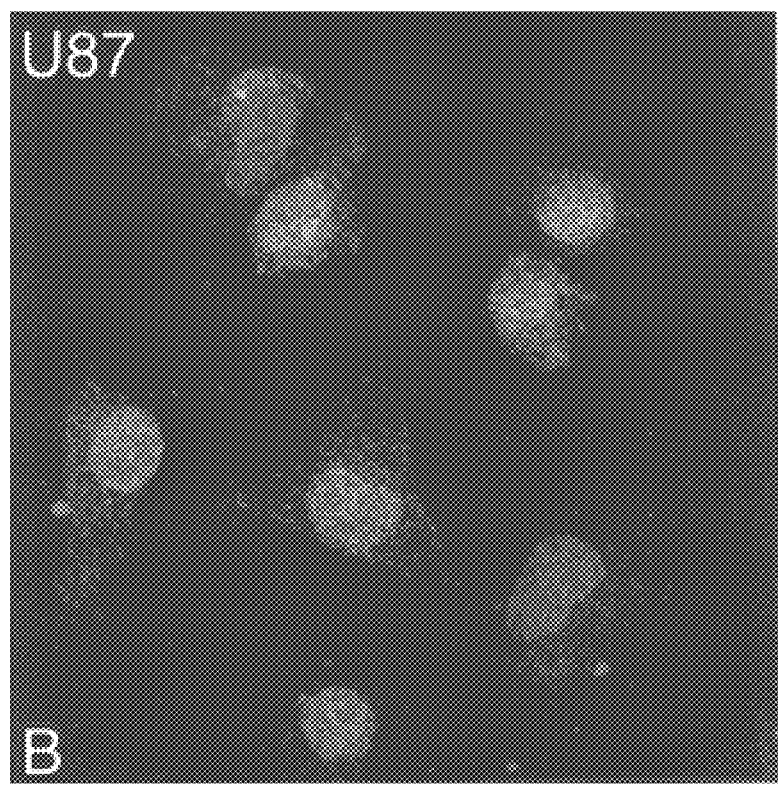

Surface expression of the EGF-R on the U373 and U87 human glioblastoma cell lines was confirmed with immunofluorescence and confocal laser scanning microscopy using monoclonal antibodies to the extracellular domain of the EGF-R. As shown in FIGS. 2a and 2b, both cell lines showed a diffuse granular immunoreactivity with the anti-EGF-R antibody.

Figure 3:
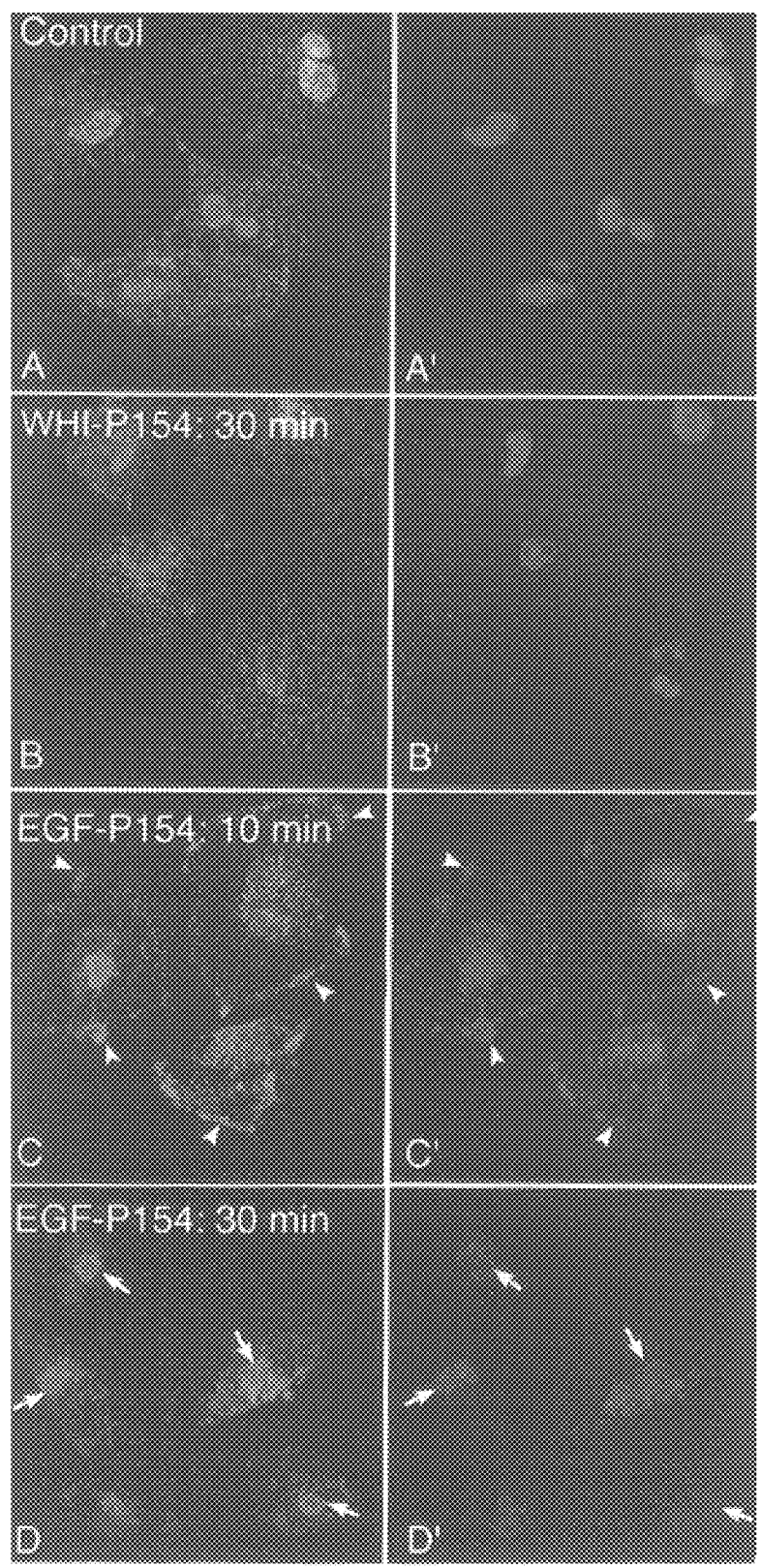
FIGS. 3A, 3A', 3B, 3B', 3C, 3C', 3D, and 3D' are photographs of immunostained cells showing EGF-R mediated uptake of EGF-P154 by U373 human glioblastoma cells.
Figure 4:
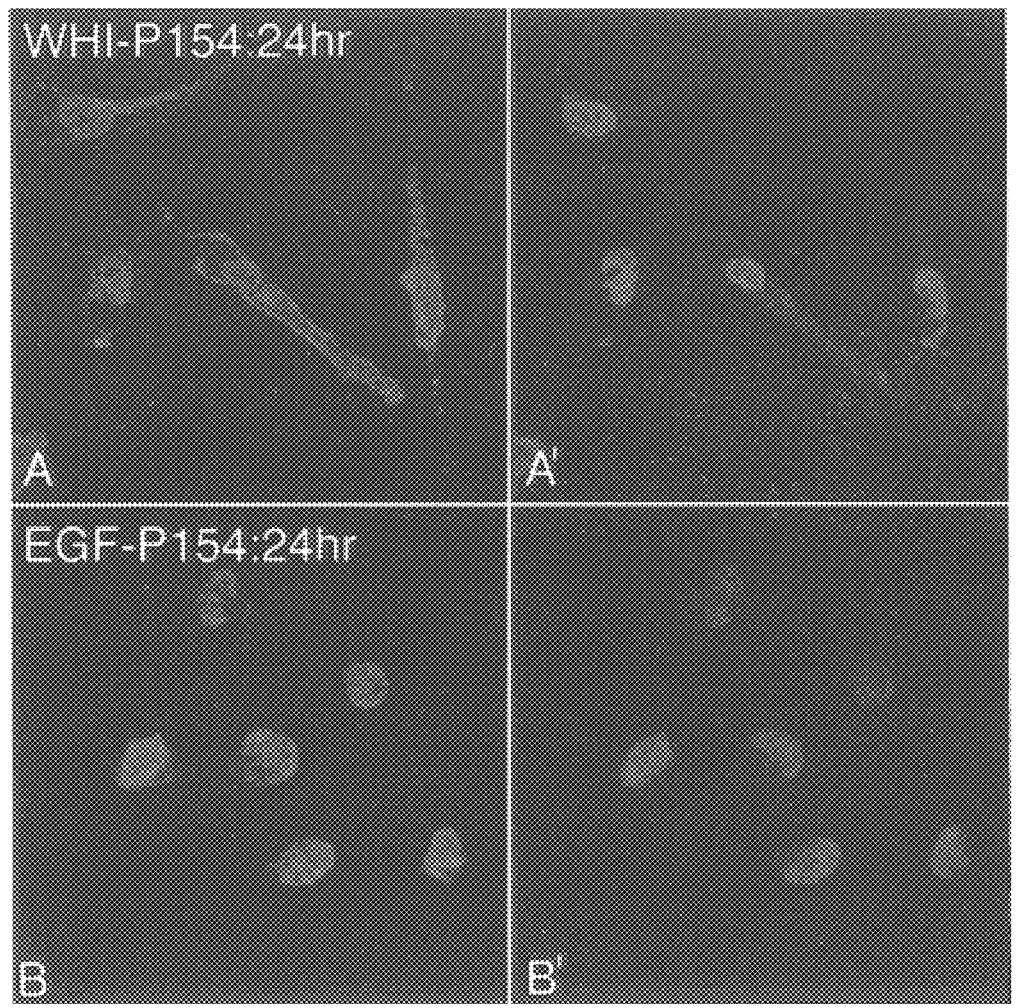
FIGS. 4A and 4B are photographs showing uptake of WHI-P154 and EGF-P154 by human glioblastoma cells.

The kinetics of uptake and cytotoxicity of the EGF-P154 conjugate in U373 glioblastoma cells were analyzed using immunofluorescence and confocal laser microscopy for following the internalized EGF-R and EGF-P154 molecules, as well as morphologic changes in treated cells. EGF-P154, similar to unconjugated EGF (not shown), was able to bind to and enter target glioblastoma cells via receptor-mediated endocytosis by inducing internalization of the EGF-R molecules. As shown in FIGS. 3A–C, 3C', 3D and 3D', within 10 minutes after exposure to EGF-P154, the EGF-R/EGF-P154 complexes began being internalized, as determined by co-localization of the EGF-R (detected by anti-EGF-R antibody, green fluorescence) and EGF-P154 (detected by anti-P154 antibody, red fluorescence) in the cytoplasm of treated cells. By 30 minutes, the internalized EGF-R/EGF-P154 complexes were detected in the perinuclear region of the treated glioblastoma cells. In contrast, cells treated with unconjugated WHI-P154 alone (FIGS. 3B, 3B') did not reveal any detectable redistribution of the surface EGF-R or cytoplasmic staining with the anti-P154 antibody (red fluorescence). By 24 hours (but not at 6 or 12 hours), WHI-154 molecules could also be detected in cells treated with unconjugated WHI-154 (FIGS. 4A, 4A', 4B, 4B'). Thus, conjugation of WHI-P154 to EGF resulted in increased uptake of this cytotoxic quinazoline derivative by EGF-R positive glioblastoma cells.

To determine if the improved delivery of WHI-P154 to glioblastoma cells by conjugation to EGF resulted in potentiation of its anti-tumor activity, the cytotoxic activities of EGF-P154 and unconjugated WHI-P154 against U373 and U87 human glioblastoma cell lines were analyzed in dose response studies using in vitro MTT assays, as described above for Example 3. As shown in FIG. 5A, EGF-P154 killed these glioblastoma cells in each of 3 independent experiments at nanomolar concentrations with mean IC50 values of 813±139 nM (Range: 588–950 nM) for U373 cells and 620±97 nM (Range: 487–761 nM) for U87 cells. The IC50 values derived from the composite cell survival curves were 881 nM for U373 cells and 601 nM for U87 cells. By comparison, unconjugated WHI-P154 killed U373 or U87 cells only at micromolar concentrations. EGF-P154 was 206-fold more potent than unconjugated WHI-P154 against U373 cells (IC50 values: 167.42±26.9 $\mu$M vs 811±139 nM, P<0.003) and 288-fold more potent than unconjugated WHI-P154 against U87 cells (IC50 values: 178.62±18.46 $\mu$M vs 620±97 nM, P<0.001) (FIG. 5A).

Figure 5B:
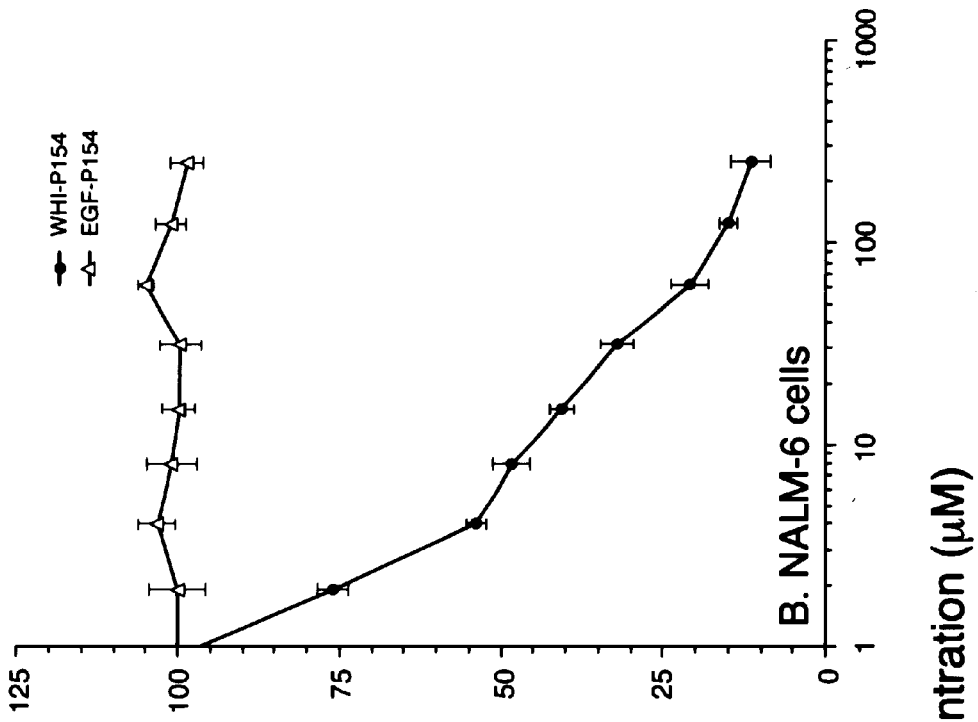
FIG. 5B shows the activity of unconjugated WHI-P154 and EGF-P154 on EGF-R negative leukemia cells.
Figure 5A:
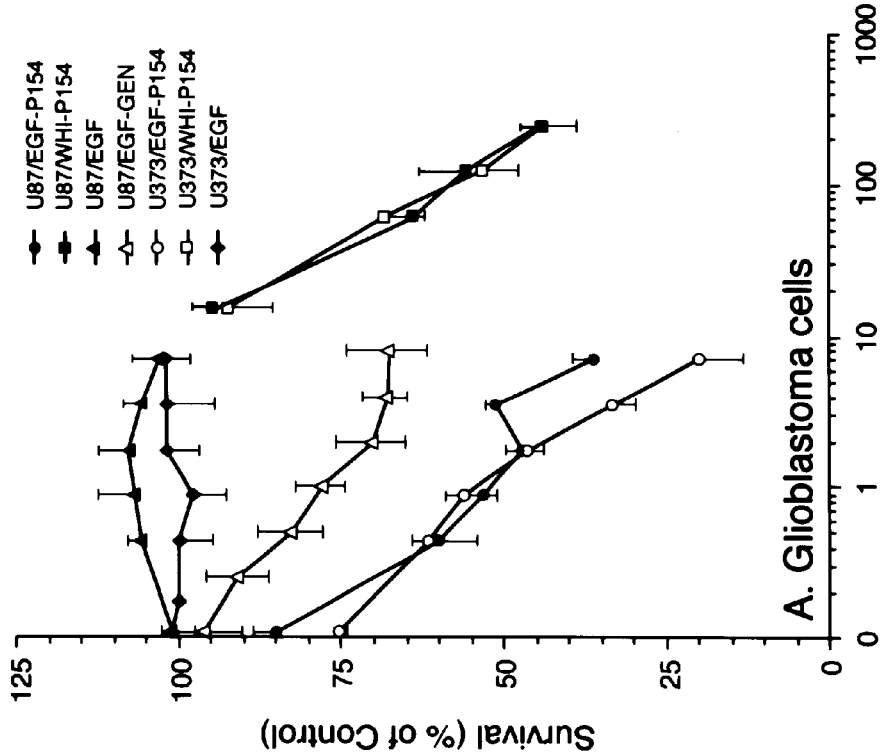
FIG. 5A is a graph demonstrating the cytotoxic activity of EGF-P154 against brain tumor cells.

Unlike WHI-P154, which showed marked cytotoxicity against the EGF-R negative NALM-6 leukemia cells, EGF-P154 elicited selective cytotoxicity to EGF-R positive glioblastoma cell lines only (FIGS. 5A and 5B). Thus, conjugation to EGF increased the potency of WHI-P154 against human glioblastoma and at the same time restricted its cytotoxicity to EGF-R positive targets.

Unlike the EGF-P154 conjugate, EGF-GEN, a potent inhibitor of the EGF-R tyrosine kinase and EGF-R associated Src family PTK, failed to kill glioblastoma cells (FIG. 5A). Thus, the potent cytotoxicity of EGF-P154 cannot be explained by the tyrosine kinase inhibitory properties of its WHI-P154 moiety.

Figure 6:
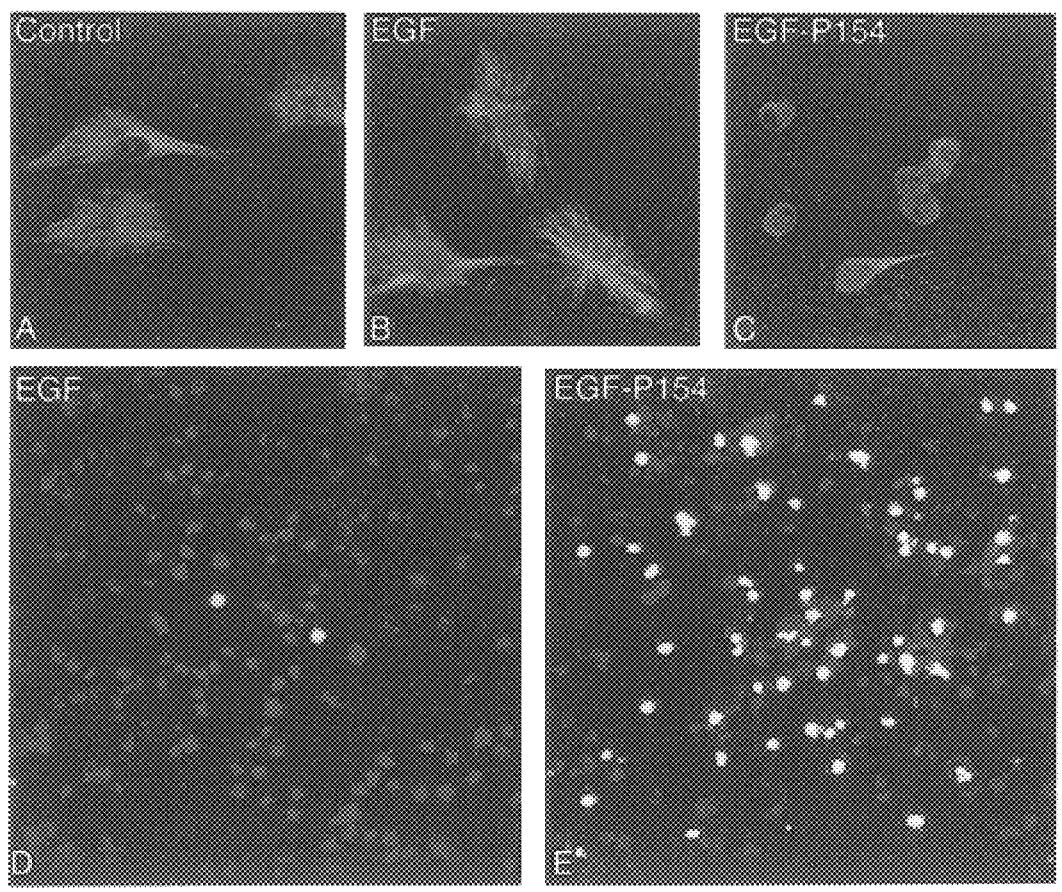
FIGS. 6A–6E are photographs showing morphological features of glioma cells treated with EGF and EGF-P154.

Immunofluorescence staining with anti-α-tubulin antibody and the nuclear dye TOTO-3 was used in combination with confocal laser scanning microscopy to examine the morphological features of U373 glioma cells treated with either unconjugated EGF or EGF-P154. As shown in FIGS. 6A–6C, after 24 hours of exposure to 25 $\mu$g/ml EGF-P154 (but not 25 $\mu$g/ml unconjugated EGF), most of the glioma cells showed an abnormal architecture with complete disruption of microtubules, marked shrinkage, nuclear fragmentation and inability to adhere to the substratum. These morphologic changes in EGF-P154-treated glioma cells were consistent with apoptosis.

To confirm apoptotic DNA fragmentation in the nuclei of EGF-P154-treated glioblastoma cells, an in situ apoptosis assay which allows the detection of exposed 3'-hydroxyl groups in fragmented DNA by TdT-mediated dUTP nick-end labeling was used. As evidenced by the confocal laser scanning microscopy images depicted in FIGS. 6D and 6E, EGF-P154 treated (but not EGF-treated) glioma cells examined for digoxigenin-dUTP incorporation using FITC-conjugated anti-digoxigenin (green fluorescence) and propidium iodide counterstaining (red fluorescence) showed many apoptotic yellow nuclei with superimposed green and red fluorescence at 36 hours after treatment.

In summary, these data demonstrate specific and enhanced cytotoxic activity of P154 when targeted to brain tumor cells by conjugation to EGF.

Example 5
Anti-tumor Activity of EGF-P154 in a SCID Mouse Model

The anti-tumor effects of conjugated EGF-P154 in vivo is demonstrated in a SCID mouse model. CB.17 SCID mice developed rapidly growing tumors after subcutaneous inoculation of $0.5 \times 10^6$ U373 cells. The in vivo anti-tumor activity of EGF-P154 in this SCID mouse xenograft model of human glioblastoma multiforme was examined.

Maintenance of SCID Mouse Colony

The SCID mice were housed in a specific pathogen-free room located in a secure indoor facility with controlled temperature, humidity, and noise levels. The SCID mice were housed in microisolater cages which were autoclaved with rodent chow. Water was also autoclaved and supplemented with trimethoprim/sulfomethoxazol 3 days/week.

SCID Mouse Xenograft Model of Human Glioblastoma

The right hind legs of the CB. 17 SCID mice were inoculated subcutaneously (s.c.) with $0.5 \times 10^6$ U373 human glioblastoma cells in 0.2 mL PBS. SCID mice challenged with brain tumor cells were treated with EGF-P154 (0.5 mg/kg/dose or 1 mg/kg/dose in 0.2 ml PBS) as daily i.p. doses for 10 treatment days starting the day after inoculation of the glioblastoma cells. Daily treatments with PBS, unconjugated EGF (1 mg/kg/dose), and unconjugated WHI-P154 (1 mg/kg/dose) were used as controls. Mice were monitored daily for health status and tumor growth, and were sacrificed if they became moribund, developed tumors which impeded their ability to attain food or water, at the end of the 3-month observation period. Tumors were measured using Vernier calipers twice weekly, and the tumor volumes were calculated according to the following formula (Friedman, S. H., mDolan, M. E., Pegg, A. E., Marcelli, S., Keir, S., Catino, J. J., Binger, D. D., Schold, S. C., Jr., 1995, Cancer Res., 55:2853–2857):

$$Volume = \frac{Width^2 * Length}{2}$$

For histopathologic studies, tissues were fixed in 10% neutral buffered formalin, dehydrated, and embedded in paraffin by routine methods. Glass slides with affixed 6 micron tissue sections were prepared and stained with hematoxylin/eosin. Primary endpoints of interest were tumor growth and tumor-free survival outcome. Estimation of life table outcome and comparisons of outcome between groups were done, as previously reported (Waurzyniak, et al., 1997, Clinical Cancer Research 3:881–890; Anderson, et al., 1995, Cancer Res. 55:1321–1327; Uckun, et al., 1997, J. Clin. Oncol. 15:2214–2221).

Results

Figure 7A:
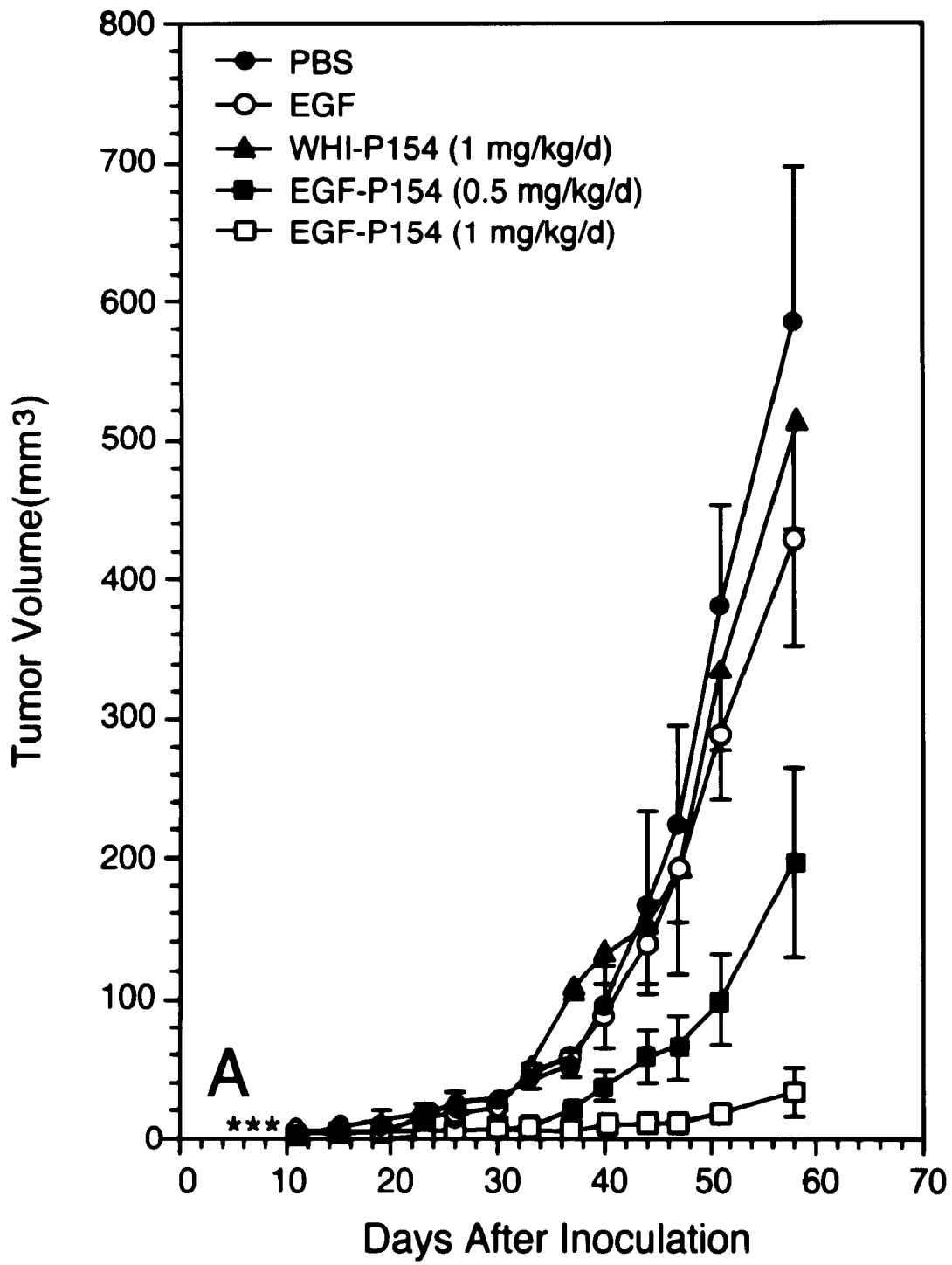
FIGS. 7A and 7B are graphs showing tumor volume and tumor-free survival times in a SCID mice human glioblastoma model treated with WHI-P154 and EGF-P154.
Figure 7B:
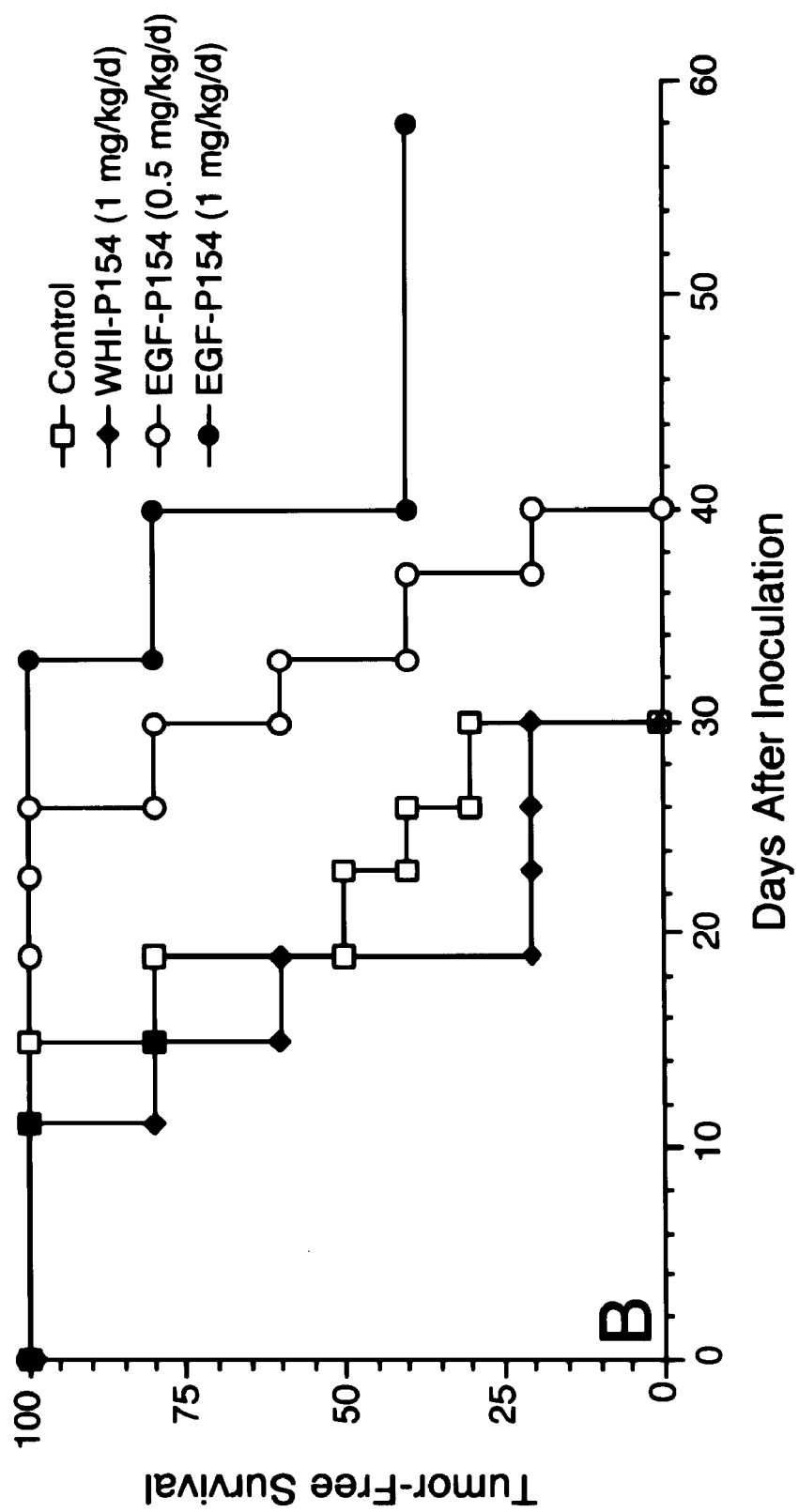

The conjugated quinazoline EGF-P154 significantly improved tumor-free survival in a dose-dependent fashion, when it was administered 24 hours after inoculation of tumor cells. FIGS. 7A and 7B show the tumor growth and tumor-free survival outcome of SCID mice treated with EGF-P154 (500 µg/kg/day×10 days or 1 mg/kg/day×10 days), unconjugated EGF (1 mg/kg/day×10 days), unconjugated WHI-P154 (1 mg/kg/day×10 days), or PBS after inoculation with U373 glioblastoma cells.

None of the 15 control mice treated with PBS (N=5; median tumor-free survival=19 days), EGF (N=5; median tumor-free survival=23 days), or unconjugated WHI-P154 (N=5; median tumor-free survival×19 days) remained alive tumor-free beyond 33 days (median tumor-free survival=19 days) (FIG. 7A). All of the 5 mice treated with EGF-P154 at the 500 µg/kg/day dose level developed tumors within 40 days with an improved median tumor-free survival of 33 days (FIG. 7B). These tumors were much smaller than those in control mice (FIG. 7A).

Tumors reached a size of 50 mm³ by 37.5±3.3 days in PBS treated mice, 34.0±3.0 days in EGF-treated mice, and 36.0±5.1 days in WHI-P154 treated mice. Tumors developing in EGF-P154 (500 µg/kg/day×10 days)-treated mice reached the 50 mm³ tumor size approximately 11 days later than the tumors in control mice treated with PBS, EGF, or WHI-P154 (47.4±7.1 days vs 35.8±1.8 days). The average size (mean±SE) of tumors at 20 days and 40 days were 10.2±1.4 mm³ and 92.3±6.0 mm³. respectively for mice in the control groups (i.e., PBS+EGF groups combined). By comparison, the average size (mean±SE) of tumors at 20 days and 40 days were significantly smaller at 1.0±1.1 mm³ (P=0.002) and 37.6±10.7 mm³ (P=0.0003) for mice treated with EGF-P154 at the 500 µg/kg/day dose level.

Notably, 40% of mice treated for 10 consecutive days with 1 mg/kg/day EGF-P154 remained alive and free of detectable tumors for>58 days (PBS+EGF+WHI-P154 vs EGF-P154, P<0.00001 by log-rank test). The tumors developing in the remaining 60% of the mice did not reach a size>50 mm³ during the 58-day observation period. Thus, EGF-P154 elicited significant in vivo anti-tumor activity at the applied nontoxic dose levels. The inability of 1 mg/kg/day×10 days of unconjugated WHI-P154 (53.2 nmol) and unconjugated EGF to confer tumor-free survival in this SCID mouse model in contrast to the potency of 1 mg/kg/day×10 days EGF-P154 (corresponding to 2.9 nmol of WHI-P154) demonstrates that the in vivo anti-tumor activity of EGF-P154 cannot be attributed to its EGF moiety alone and also that conjugation to EGF enhances the in vivo anti-tumor activity of WHI-P154 against glioblastoma cells by>18-fold.

Taken together, the findings of Examples 3–5 provide unprecedented evidence that the substituted quinazoline 3-bromo-4'-hydroxylphenyl)-amino-6,7-dimethoxyquinazoline (WHI-P154) exhibits significant cytotoxicity against human glioblastoma cells and that its anti-tumor activity can be substantially enhanced by conjugation to EGF as a targeting molecule. Although WHI-P154 is a potent inhibitor of the EGF-R kinase as well as Src family tyrosine kinases, its cytotoxicity in glioblastoma cells cannot be attributed to its tyrosine kinase inhibitory properties alone, since 4-(3 '-Bromophenyl)-amino-6,7-dimethoxyquinazoline (WHI-P79) with equally potent PTK inhibitory activity, failed to kill WHI-P154 sensitive glioblastoma cells. Similarly, several PTK inhibitors capable of killing human leukemia and breast cancer cells lacked detectable cytotoxicity against glioblastoma cells. Glioblastoma cells exposed to EGF-conjugated WHI-P154 underwent apoptosis. Although EGF was used to target WHI-P154 to glioblastoma cells in the present study, other biologic agents including different cytokines such as IGF and antibodies reactive with glioblastoma—associated antigens are also expected to be effective targeting molecules for this novel quinazoline derivative.

Example 6

Substituted Quinazolines Inhibit Glioblastoma Cell Adhesion

During the multistep process of tissue invasion, tumor cells initially adhere to the extracellular matrix proteins via cell surface integrin receptors and then gain migratory capacity to enter the surrounding tissues. ECM proteins such as laminin, fibronectin, and type IV collagen are thought to play an important role in tumor cell attachment and migration. Laminin, fibronectin and collagen have been found in the basal lamina of blood vessels and in the glial limitans externa in the brain that promote the adhesion and invasion of tumor cells in situ (Carbonetto, S., 1984, Trends Neurosci., 7:382–387; Rutka, J. T., Apodaca, G., Stern, R., J. Neurosurg., 69:155–170; Venstrom, K. A. and Reichard, L. F., 1993, FASEB J., 7:996–1003). The effects of these ECM proteins on integrin-mediated glioblastoma cell adhesion was examined using four different human glioblastoma (U87, U373, T98, and U138) and one medulloblastoma (Daoy) cell line.

Cell Lines

Human brain tumor cell lines derived from adult patients with glioblastoma, U-87 MG (Cat.#HTB-14), U-118 MG (Cat. #HTB-15), U-138 MG (Cat. #HTB 16), U-373 MG (Cat. #HTB-17), T98-G (Cat. #CRL-1690) and medulloblastoma Daoy (Cat. #HTB-186) were obtained from American Type Culture Collection (ATCC, Rockville, Md.) and maintained in liquid culture using DMEM supplemented with 10% fetal bovine serum and antibiotics. Fibroblast conditioned medium was used as a source of chemoattractant in vitro invasion assays. Conditioned medium was prepared as described previously (Albini, A., Iwamoto, Y., Kleinman, H. K., Martin, G. R., Aaronson, S. A., Kozlowski, J. M., and McEwan, R. N., 1987, *Cancer Res.*, 47:3239–3245). For the preparation of this conditioned medium NIH/3T3 embryonic fibroblasts (AATCC cat. #CRL-1658) were grown to 80% confluency in DMEM medium supplemented with 10% FBS and cultured for 24 hours in serum-free medium containing 0.5 $\mu$g/ml bovine serum albuminutes The culture supernatants were collected, centrifuged at 1000×g for 15 minutes to remove cellular debris and used as conditioned medium.

Adhesion Assays

In vitro adhesion assays were performed to (a) study the baseline adhesive properties of various glioblastoma cell lines and (b) evaluate the effects of quinazoline derivatives on the adhesive properties of glioblastoma cells. The plates for the adhesion assays were precoated with the extracellular matrix proteins laminin, fibronectin or type IV collagen (each at a final concentration of 1 $\mu$g/ml in PBS) overnight at 4° C. and dried. On the day of the experiment, the wells were rehydrated and blocked with 10% bovine serum albumin in PBS for 1 hour at room temperature and used for the adhesion assays, as described below.

To study the effects of quinazoline derivatives on glioblastoma cell adhesion, exponentially growing cells in DMEM were incubated with the compounds WHI-P79, WHI-P97, WHI-P31, WHI-P154, WHI-P258 or genistein at concentrations ranging from 1 $\mu$M to 100 $\mu$M for 16 hours in a humidified 5% $CO_2$ atmosphere. DMSO (0.1%) was included as a vehicle control. After treatment, cells were detached from the flasks with 0.05% trypsin (Life Technologies) resuspended in DMEM, incubated at 37° C. for 2 hours to allow them to recover from the trypsinization stress and examined for their ability to adhere to plates precoated with ECM proteins.

In adhesion assays, cells were centrifuged, washed twice with serum-free DMEM, counted and resuspended in serum-free DMEM to a final concentration of $2.5 \times 10^5$ cells/ml. One hundred $\mu$l of the cell suspension containing $2.5 \times 10^4$ cells were added to each well and cells were allowed to adhere for 1 hour at 37° C. in a humidified 5% $CO_2$ atmosphere. The adherent fraction was quantitated using MTT (3-[4,5-dimethulthiazol-2-yl]-2,5-diphenyltetrazolium bromide) assays. In brief, after washing the wells, 10 $\mu$l of MTT (0.5 mg/ml final concentration) (Boehringer Mannheim Corp., Indianapolis, Ind.) was added to each well and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbance of each well was measured in a microplate reader (Labsystems) at 540 nm and a reference wavelength of 690 nm. To translate the $OD_{540}$ values into the number of cells in each well, the $OD_{540}$ values were compared to those on standard $OD_{540}$-versus-cell number curves generated for each cell line. The adherent fractions of cells treated with quinazoline derivatives were compared to those of DMSO-treated control cells and the percent inhibition of adhesion was determined using the formula:

$$\% \text{ Inhibition} = 100 * \frac{1 - \text{Adherent Fraction of Drug Treated Cells}}{\text{Adherent Fraction of Control Cells}}$$

Each treatment condition was evaluated in duplicate in 3 independent experiments. The IC50 values were calculated by non-linear regression analysis.

Results

Figure 8:
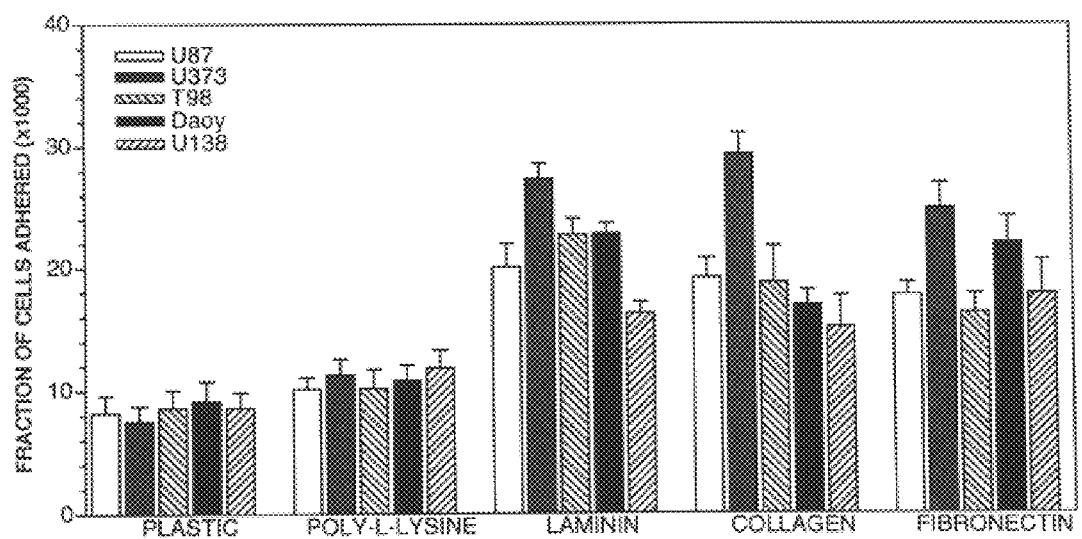
FIG. 8 is a bar graph showing adhesion of glioblastoma and medulloblastoma cells to plates coated with various ECM proteins.
Figure 9A:
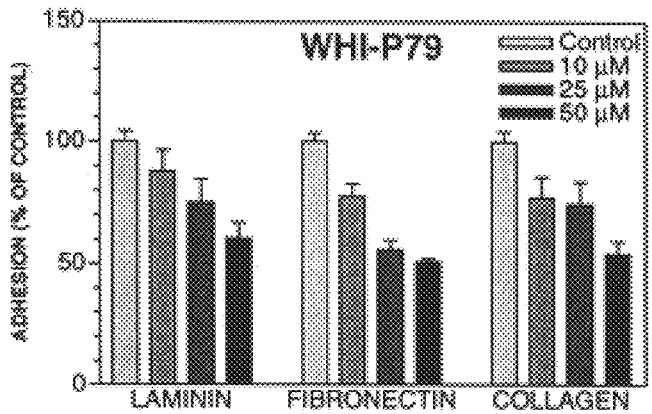
FIGS. 9A–9D are bar graphs showing inhibition of cell adhesion to ECM proteins in the presence of the compounds of the invention.
Figure 9B:
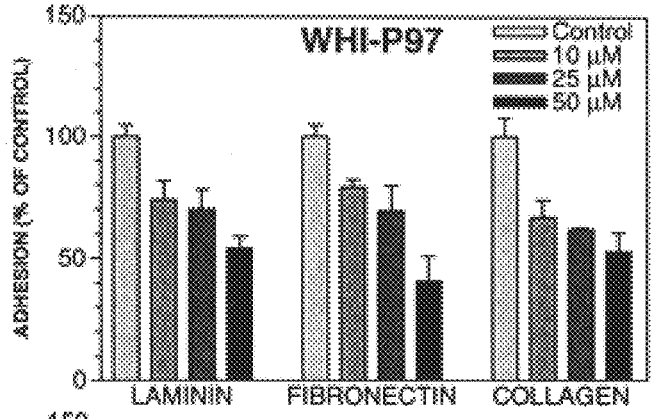
Figure 9C:
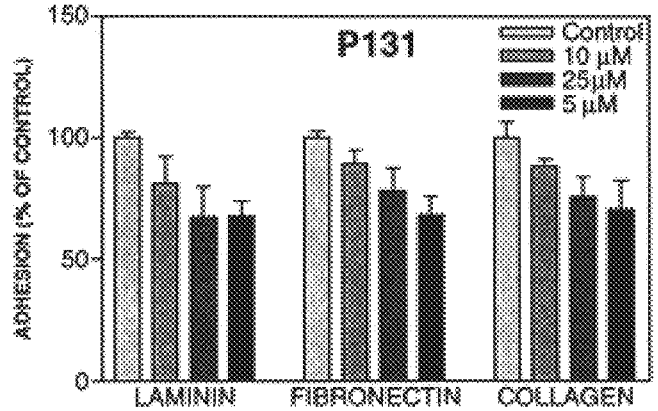
Figure 9D:
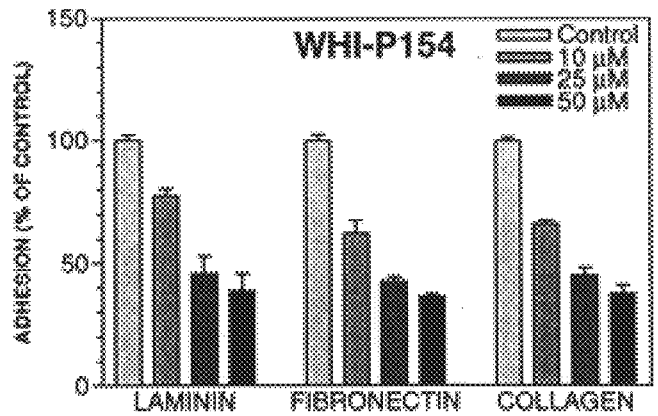

As shown in FIG. 8, a significantly greater fraction of glioblastoma and medulloblastoma cells adhered to plates precoated with laminin, type IV collagen, or fibronectin than to uncoated or poly-L-lysine-coated control plates. Of the four glioblastoma cell lines examined, U373 cells were the most adhesive. Therefore, U373 cells were used in subsequent experiments that were designed to examine the effects of various quinazoline derivatives on integrin-mediated glioblastoma cell adhesion.

As shown in FIGS. 9A–9D, the novel quinazoline derivative 4-(3'-Bromo-4'-hydroxylphenyl)-amino-6,7-dimethoxyquinazoline (WHI-P154) (but not the unsubstituted parent compound WHI-P258) inhibited the adhesion of U373 cells to laminin-, fibronectin-, and collagen-coated plates in a dose-dependent fashion with mean IC50 values of 29.8±3.1 $\mu$M (N=3) for adhesion to fibronectin-coated plates, 36.1±3.5 $\mu$M (N=3) for adhesion to laminin-coated plates, and 42.7±2.5 $\mu$M (N=3) for adhesion to collagen-coated plates. The 3'-bromo substitution on the phenyl ring likely contributes to the activity of WHI-P154 since 4-(4'-hydroxylphenyl)-amino-6,7-dimethoxyquinazoline [WHI-P131] lacking this bromo substituent was less potent than WHI-P154 (all IC50 values:>50 $\mu$M). The 4'-hydroxyl substituent on the phenyl ring also contributed to the inhibitory activity of WHI-P154 since 4-(3'-Bromophenyl)amino-6,7-dimethoxyquinazoline [WHI-P79] which differs from WHI-P154 only by the lack of the 4'-hydroxyl group on the phenyl ring, was less potent (all IC50 values: >50 $\mu$M). Introduction of a second bromo group at the 5' position of the phenyl ring did not result in improved inhibitory activity: 4-(3',5'-Dibromo-4'-hydroxylphenyl)amino-6,7-dimethoxyquinazoline [WHI-P97] was not more potent than WHI-P154.

Example 7

Effect of WHI-P154 on EGF-induced Cell Adhesion

In addition to binding of cell surface receptors to ECM proteins and integrin clustering, formation of focal adhesion plaques is also regulated by the activation of focal adhesion kinase by certain growth factors upon binding to their receptors (Hatai, M., Hashi, H., Mogi, A., Soga, H., Yokota, J., Yaoi, Y., 1994, *FEBS Lett.*, 350:113–116; Ouwens, D. M., Mikkers, H. M., van der Zon, G. C., Stein Gerlach, M., Ullrich, A., Maassen, J. A., 1996, *Biochem J.* 318:609–614; Schaller, M. D., Parsons, J. T., *Curr. Opin. Cell*; Zachary, I., 1997, *Int. J. Biochem., Cell Biol.*, 29:929–934). EGF is a potent mitogen for various brain tumor cells that express EGF receptor and are also shown to modulate the expression of cell surface To study the effects of quinazoline derivatives on EGF-stimulated cell adhesion, the trypsinized and recovered cells were incubated with varying concentrations ranging from 1 $\mu$M to 50 $\mu$M of quinazolines for 4 hours at 37° C., then stimulated with 250 $\mu$ng/ml of EGF and examined for their ability to adhere to poly-L-lysine coated plates.

For the EGF stimulation experiments, the cells were plated in the presence of 250 $\mu$ng/ml of EGF and allowed to adhere for 1 hour. The non-adherent cells were removed by gently washing the cells with PBS and then the adherent fraction was quantitated as described above for Example 6.

Figure 10:
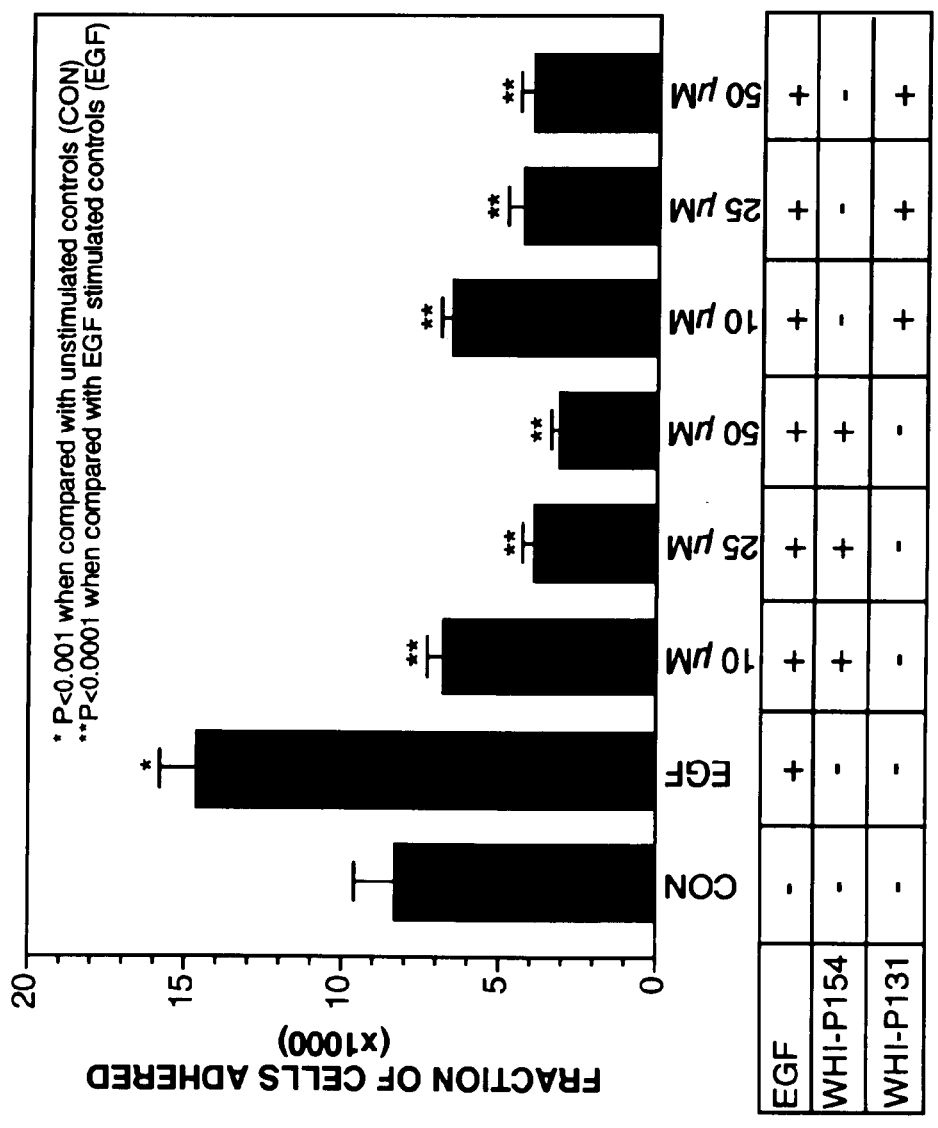
FIG. 10 is a graph showing the inhibition of EGF-induced cell adhesion in the presence of the compounds of the invention.

Stimulation of U373 cells with EGF significantly increased the fraction capable of adhering to poly-L-lysine coated plates from 33.2±5.2% to 58.48±4.7% (P<0.02). A four-hour pretreatment of U373 cells with WHI-P154 not only completely prevented the EGF-induced adhesion but it also reduced the adhesive fraction of U373 cells in a dose-dependent fashion far below the baseline levels despite the presence of EGF (FIG. 10). Similar, albeit less potent, inhibitory effects were observed when cells were pretreated with WHI-P131.

Example 8
Substituted Quinazolines Inhibit Glioblastoma Cell Invasion Glioblastoma Cell Invasion Through Matrigel Matrix The in vitro invasiveness of glioblastoma cells was assayed using a previously published method which employs Matrigel-coated Costar 24-well transwell cell culture chambers ("Boyden chambers") with 8.0-μm-pore polycarbonate filter inserts (Albini, A., Iwamoto, Y., Kleinman, H. K., Martin, G. R., Aaronson, S. A., Kozlowski, J. M., and McEwan, R. N., 1987, *Cancer Res.*, 47:3239–3245). The chamber filters were coated with 50 μg/ml of Matrigel matrix, incubated overnight at room temperature under a laminar flow hood and stored at 4° C. Matrigel matrix is made up of several components of the extracellular matrix (ECM), including collagens, laminin and proteo-glycans On the day of the experiment, the coated inserts were rehydrated with 0.5 ml serum-free DMEM containing 0.1% bovine serum albumin for 1–2 hours. To study the effects of quinazoline derivatives on invasiveness of glioblastoma cells, exponentially growing cells were incubated overnight with WHI-P97, WHI-P131 and WHI-P154 at various concentrations ranging from 1 μM to 50 μM. The cells were trypsinized, washed twice with serum-free DMEM containing BSA, counted and resuspended at $1\times10^5$ cells/ml. 0.5 ml cell suspension containing $5\times10^4$ cells in a serum-free DMEM containing quinazoline compounds or vehicle was added to the Matrigel-coated and rehydrated filter inserts. Next, 750 μl of NIH fibroblast conditioned medium was placed as a chemoattractant in 24-well plates and the inserts were placed in wells and incubated at 37° C. for 48 hours. After the incubation period, the filter inserts were removed, the medium was decanted off and the cells on the top side of the filter that did not migrate were scraped off with a cotton-tipped applicator. The invasive cells that migrated to the lower side of the filter were fixed, stained with Hema-3 solutions and counted under microscope. Five to 10 random fields per filter were counted to determine the mean (±SE) values for the invasive fraction. The invasive fractions of cells treated with quinazoline derivatives were compared to those of DMSO treated control cells and the percent inhibition of invasiveness was determined using the formula:

$$\% \text{ Inhibition} = 100 \left[ \frac{1 - \text{Adherent Fraction of Drug Treated Cells}}{\text{Adherent Fraction of Control Cells}} \right]$$

Each treatment condition was evaluated in duplicate in 3 independent experiments. IC50 values were calculated by non-linear regression analysis using Graphpad Prisin Software Version 2.0 (Graphpad Software Inc., San Diego, Calif.).

Results

Figure 11A:
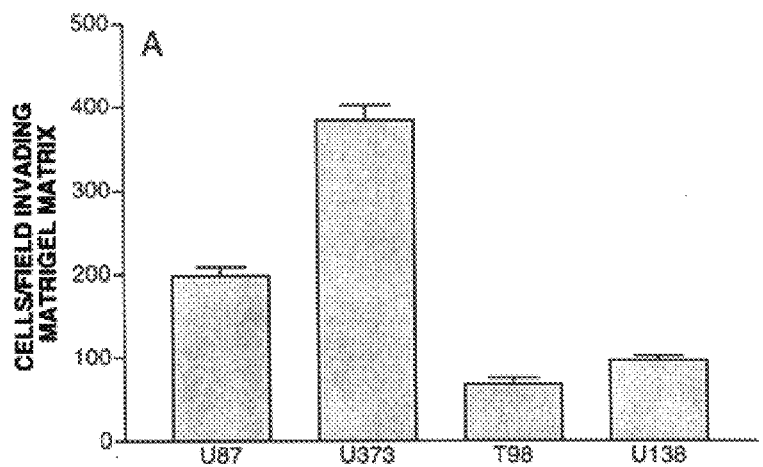
FIGS. 11A and 11B are graphs demonstrating inhibition of brain tumor cell migration through the extracellular matrix MATRIGEL Matrix in the presence of the compounds of the invention.
Figure 11B:
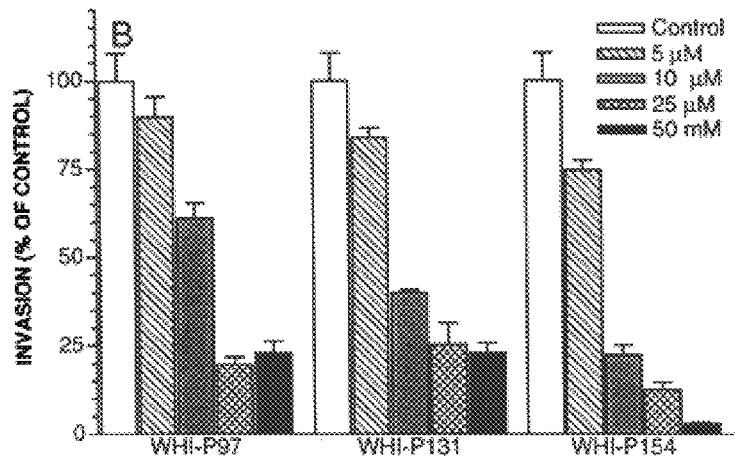

As shown in FIG. 11, U373 glioblastoma cells were highly invasive in Matrigel-coated Boyden chambers. WHI-P154 inhibited the invasion of U373 cells through the Matrigel matrix in dose-dependent fashion and it was more potent than WHI-P131 or WHI-P97 (FIG. 11). The mean IC50 values obtained from 3 independent experiments were 10.59±1.8 μM (range: 9.57–11.64 μM) for WHI-P97, 7.07±1.8 μM (range 5.08–8.59 μM) for WHI-P131, and 4.46±0.8 μM (range: 3.53–5.01) for WHI-P154. The IC50 values derived from the average values of three experiments were 9.58 μM for WHI-P97, 7.95 μM for WHI-P131 and 5.2 μM for WHI-P154.

Example 9
Substituted Quinazolines Inhibit Focal Adhesion Plaques and Actin Polymerization Cytoskeletal organization and cellular adhesion are two crucial determinants of cell motility and these processes are controlled by the complex coordination of actin cytoskeletal rearrangement and changes in focal adhesions (Symons, M. H., and Mitchison, T. J., 1991, *J. Cell Biol.*, 114:503–513; Wang, Y. L., 1984, *J. Cell Biol.*, 99:1478–1485; Bretcher, M. S., 1996, *Cell*, 87:601–606; Machesky, L. M. and Hall. A., 1997, *J. Cell Biol.*, 138:913–926). Polymerization of actin filaments, formation of lamellepodia and filapodia at the leading edges are essential for the attachment and detachment of cells from the ECM and play pivotal roles in cell motility and migration (Burridge, K., Fath, K., Kelly, G., and Turner, C., 1988, *Ann. Rev. Cell Biol.*, 4:487–525; Burridge, K., Nuckolls, C., Otey, F., Pavalko, K., Simon, K., and T Aumer, C., 1990, *Cell Differ. Dev.*, 32:337–342). Formation of adhesion plaques is also important in this process because the polymerized actin fibers are tethered and linked to ECM at these junctions and the cell movement is dependent on the strength of these focal adhesions. Moderate level of cellular adhesive strength is thought to be necessary for cell migration (Burridge, K., Fath, K., Kelly, G., and Turner, C., 1988, *Ann. Rev. Cell Biol.*, 4:487–525; Burridge, K., and Fath, K., 1989, *Bioessays*, 10:104–108; Schwarzbauer, J. E., 1997, *Curr. Biol.*, 7:292–294). Adhesions that are too strong may impair cell motility and adhesions that are too weak may not provide sufficient momentum to move the cell forward.

EGF-induced cell adhesion is brought about by enhanced formation of $FAK^+/Actin^+$ focal adhesion plaques, which is triggered by redistribution of activated FAK. EGF-induced formation of focal adhesions in serum-starved U373 cells was examined by multicolor immunofluorescence and confocal laser scanning microscopy using a murine monoclonal anti-FAK antibody (green fluorescence) and rhodamine-labeled phalloidin which stains actin (red fluorescence).

To evaluate the actin polymerization process, cells plated on poly-L-lysine-coated plates were first serum-starved to depolymerize the actin stress fibers. Subsequently, cells were stimulated with fetal bovine serum to induce de novo stress fiber formation.

Fluorescence Microscopy

Immunofluorescence was used to study the effects of quinazoline derivatives on the formation of focal adhesion plaques and polymerization of actin. Cells (obtained and maintained as described for Example 6) were plated on poly-L-lysine-coated glass-bottom 35 mm Petri dishes (Mattek Corp., Ashland, Mass.) or fibronectin-coated cover slips and maintained in DMEM supplemented with 10% FBS for 24 hrs. The medium was removed and the cells were washed twice with serum-free DMEM and incubated in the same medium for 16 hours. Following this serum starvation, cells were incubated with varying concentrations of WHI-P131, WHI-P154 or vehicle (0.1% DMSO) for 4–16 hours at 37° C. and then stimulated either with 250 μng/ml of human recombinant EGF or 10% FBS for 15, 30, 60, 120 or 180 minutes at 37° C. At the end of the EGF stimulation, cells were washed twice with PBS, fixed in 2% paraformaldehyde in PBS (pH 7.2), permeabilized and non-specific binding sites were blocked with 1.5% BSA and 0.1% triton X-100 in PBS for 30 minutes.

To detect the focal adhesion plaques and actin, cells were incubated with a mixture of a mouse monoclonal antibody directed against the focal adhesion kinase at a dilution of 1:100 and rhodamine-labeled phalloidin at a dilution of 1:1000 for 1 hour at room temperature. Cells were washed with PBS and incubated with a FITC-conjugated anti-mouse IgG (Amersham Corp., Arlington Heights, Ill.) for 1 hour (final dilution: 1:40). Cells were washed with PBS, counterstained with TOTO-3 (Molecular Probes, INC.) at a dilution of 1:1000 for 10 minutes at room temperature, washed again with PBS and the coverslips were counted with Vectashield (Vector Labs, Burlingame, Calif.). Subsequently, cells were viewed with a confocal laser scanning microscope (Bio-Rad MRC 1024) mounted in a Nikon Labhophot upright microscope. Digital images were saved on a Jaz disk and processed with Adobe Photoshop software (Adobe systems, Mountain View, Calif.). Prism software. Each experiment was repeated three times.

Results

Figure 12:
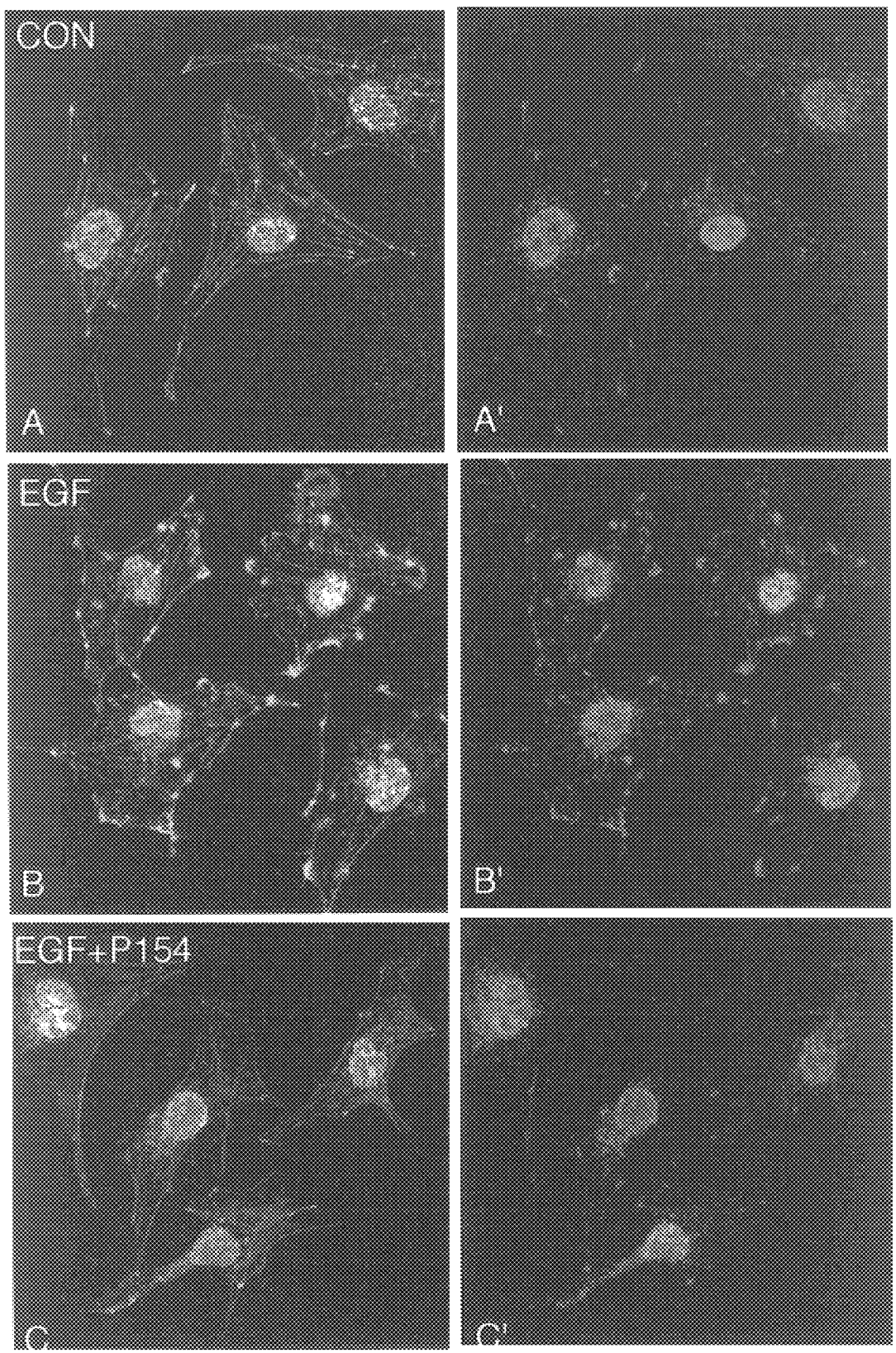
FIGS. 12A–C and 12A'–C' are photographs of immunostained cells demonstrating the inhibition of focal adhesion complex formation in glioblastoma cells in the presence of the compounds of the invention.

As shown in FIGS. 12A, 12A', 12B, 12B', 12C, 12C', a two-hour stimulation of serum-starved U373 cells with EGF resulted in a significant decrease of the diffuse perinuclear/cytoplasmic FAK staining accompanied by the emergence of focal adhesion plaques with high intensity FAK staining (bright green fluorescence). These $FAK^+$ adhesion plaques showed a strong phalloidin staining (bright red fluorescence) confirming the colocalization of actin. Notably, preincubation of U373 cells with WHI-P154 (FIG. 12B) or WHI-P131 (data not shown) at a 10 $\mu$M concentration prevented the formation of $FAK^+/Actin^+$ focal adhesion plaques after EGF stimulation.

Figure 13:
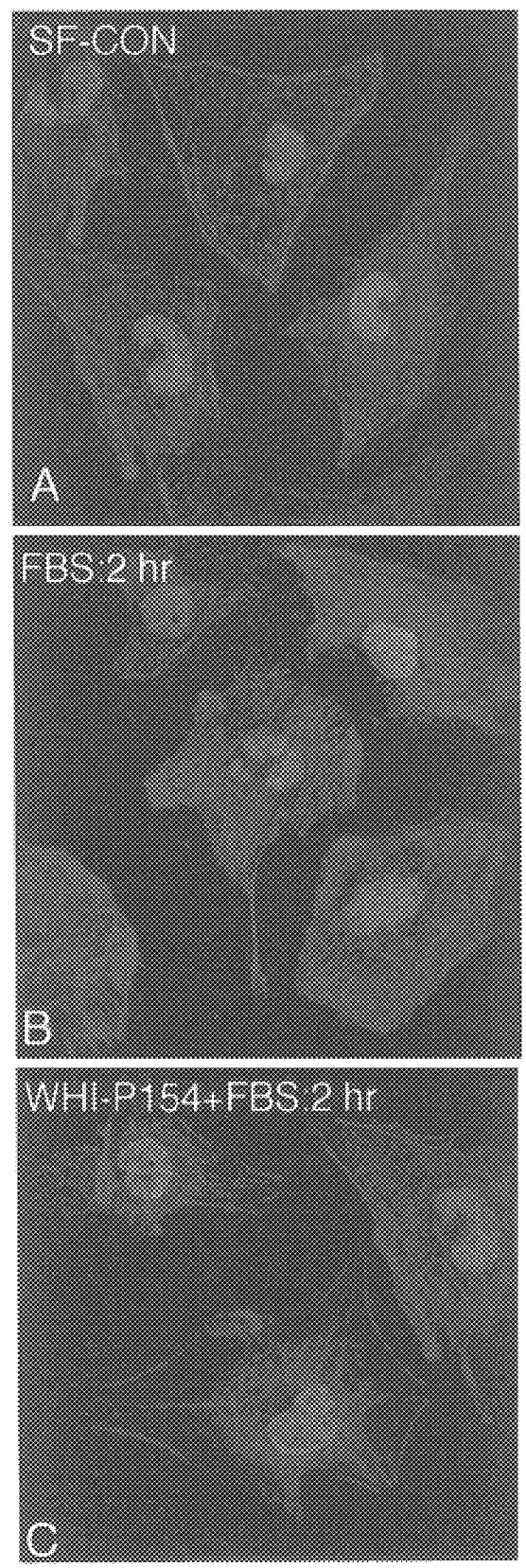
FIGS. 13A–13C are photographs of immunostained cells demonstrating the inhibition of actin stress fiber formation in glioblastoma cells contacted with the compounds of the invention.

To evaluate the actin polymerization process, cells plated on poly-L-lysine-coated plates were first serum-starved to depolymerize the actin stress fibers. Subsequently, cells were stimulated with fetal bovine serum to induce de novo stress fiber formation. As shown in FIG. 13A–C, a two-hour stimulation of serum-starved U373 cells with fetal bovine serum (10% v/v) resulted in a marked increase in polymerized actin stress fibers. Pretreatment of serum-starved U373 cells with WHI-P154 inhibited serum-induced actin polymerization (FIG. 13C). Similar results were obtained with WHI-P131 but not with the unsubstituted dimethoxy quinazoline compound WHI-P258 (data not shown).

In summary, the data provided in Examples 6–9 demonstrate the effectiveness of substituted quinazolines in the inhibition of glioblastoma cell adhesion and migration, key factors for tumor cell metastasis. The most potent inhibitory agents were WHI-P154 and WHI-P131. Both compounds inhibited adhesion and migration at micromolar concentration.

A complex network of intracellular molecules including receptor tyrosine kinases and Src family tyrosine kinases in cooperation with several extracellular factors such as substratum to which cells adhere and external factors, regulates the cell adhesion and motility (Finchman, V. J., and Frame, M. C., 1998, *EMBO J.*, 17:81–92). Activation of integrin family adhesion receptors upon binding to specific extracellular matrix proteins has been shown to enhance the phosphorylation of integrins and activation of several intracellular signaling proteins including mitogen activated protein kinase, FAK, Src tyrosine kinases as well as $p130^{cas}$, talin, paxillin, and cortactin which were identified as substrates for the Src tyrosine kinase (Cobb, B. S., Schaller, M. D., Leu, T. H., and Parsons, J. T., 1994, *Mol. Cell Biol.*, 14:147–155; Chen, Q., Lin, T. H., Der. C. J., Juliano, R. L., 1996, *J. Biol. Chem.*, 271:18122–18127; Klemke, R. L., Cai, S., Giannini, A. L., Gallagher, P. J., Lanerolle, P. D., and Cheresh, D. A., 1997, *J. Cell Biol.*, 137:481–492; Petch, L. A., Bockholt, S. M., Bouton, A., Parsons, J. T., Burridge, K., 1995, *J. Cell Sci.*, 108:1371–1379; Chrzanowska-Wodnicka, M., and Burridge, K., 1996, *J. Cell Biol.* 133(6):1403–15; Miyamoto, S., Akiyama, S. K., Yamada, K. M., 1995, *Science*, 267:883–5; Miyamoto, S., Teramoto, H., Gutkind, J. S., and Yamada, K. M., 1996, *J. Cell Biol.*, 135:1633–1642; Chen, H. C., Appeddu, P. A., Parsons, J. T., Hildebrand, J. D., Schaller, M. D., and Guan, J. L., 1995, *J. Biol. Chem.I*, 16995–16999). Subsequently, the adhesion of cell is strengthened by redistribution of activated Src kinase and focal adhesion kinase to focal adhesions, recruitment and aggregation of activated intracellular proteins such as paxillin, talin, viniculin and clustering of integrins (Burridge, K., Fath, K., Kelly, G., and Turner, C., 1988, *Ann. Rev. Cell Biol.*, 4:487–525; Burridge, K., and Fath, K., 1989, *Bioessays*, 10:104–108; Finchman, V. J., and Frame, M. C., 1998, *EMBO J.*, 17:81–92). FAK is also activated by the binding of certain growth factors to their receptors in a mechanism that is independent of integrin activation (Hatai, M., Hashi, H., Mogi, A., Soga, H., Yokota, J., Yaoi, Y., 1994, *FEBS Lett.*, 350:113–116; Ouwens, D. M., Mikkers, H. M., van der Zon, G. C., Stein Gerlach, M., Ullrich, A., Maassen, J. A., 1996, *Biochem J.*, 318:609–614).

In experiments not shown here, WHI-P154 was found to be a potent inhibitor of the EGF-R tyrosine kinase as well as Src family tyrosine kinases (Liu and Uckun, manuscript in preparation). Therefore, it was initially postulated that the effects of WHI-P154 on glioblastoma cells was due to its tyrosine kinase inhibitory properties. Surprisingly, however, WHI-P79 and WHI-P131, which are equally potent inhibitors of the EGF-R and Src family tyrosine kinases were not as effective as WHI-P154 and the broad spectrum tyrosine kinase inhibitor genistein did not affect glioblastoma cell adhesion and motility at concentrations which abrogate the enzymatic activity of the EGF-R kinase and Src family tyrosine kinases. Thus, the effects of WHI-P154 on U373 cells cannot be explained by its tyrosine kinase inhibitory properties alone.

Example 10

WHI-P154 Inhibits Glioblastoma Cell Migration from Spheroids

U373 glioblastoma spheroids of 200 to 400 micrometers in diameter were treated with WHI-P154 in 0.1% DMSO at varied concentrations. Cells were incubated with the inhibitor or with control DMSO in the absence of inhibitor compound for two hours, and then transferred to fibronectin-coated coverslips. The spheroids were then incubated in DMEM containing WHI-P154 at 37° C. for 48 hours.

Figure 14:
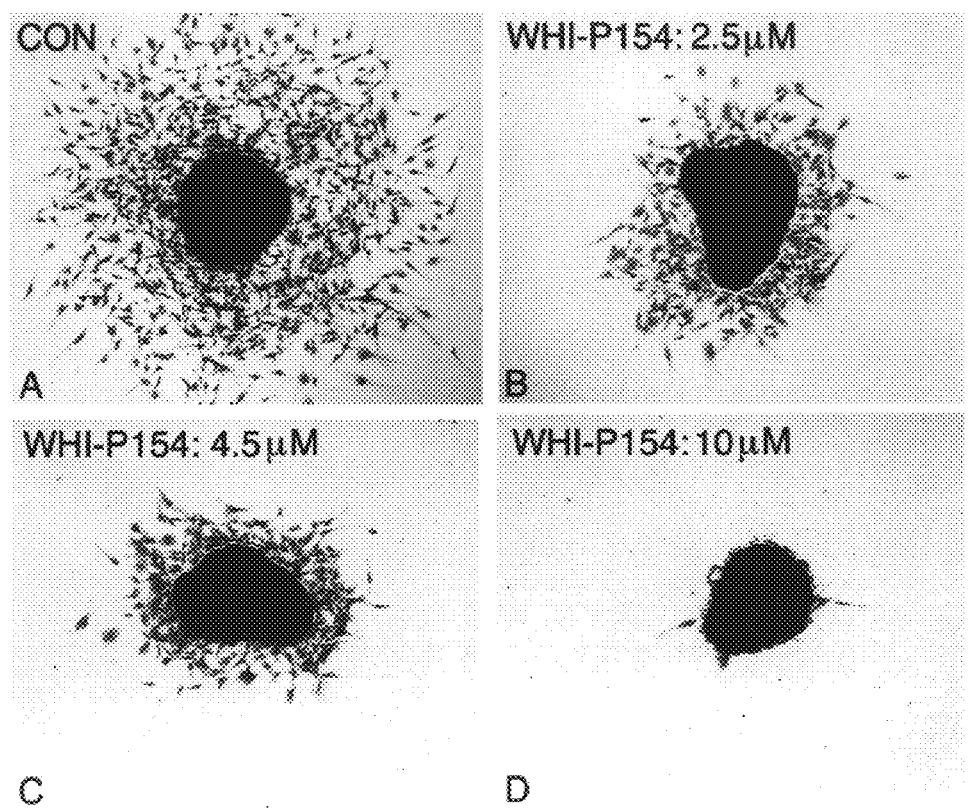
FIGS. 14A–D are photographs showing inhibition of tumor cell outgrowth from glioblastoma spheroids in the presence of the compounds of the invention.

As shown in FIGS. 14 A–14D, treatment of glioblastoma spheroids with WHI-P154 significantly inhibited cell migration from the spheroid as compared with the untreated control and in a dose-dependent manner. The Figure shows the following dosage treatments: A: control; B: 2.5 $\mu$M; C: 4.5 $\mu$M; and D: 10 $\mu$M.

Example 11

Cytotoxic Activity of WHI-P292

Figure 15:
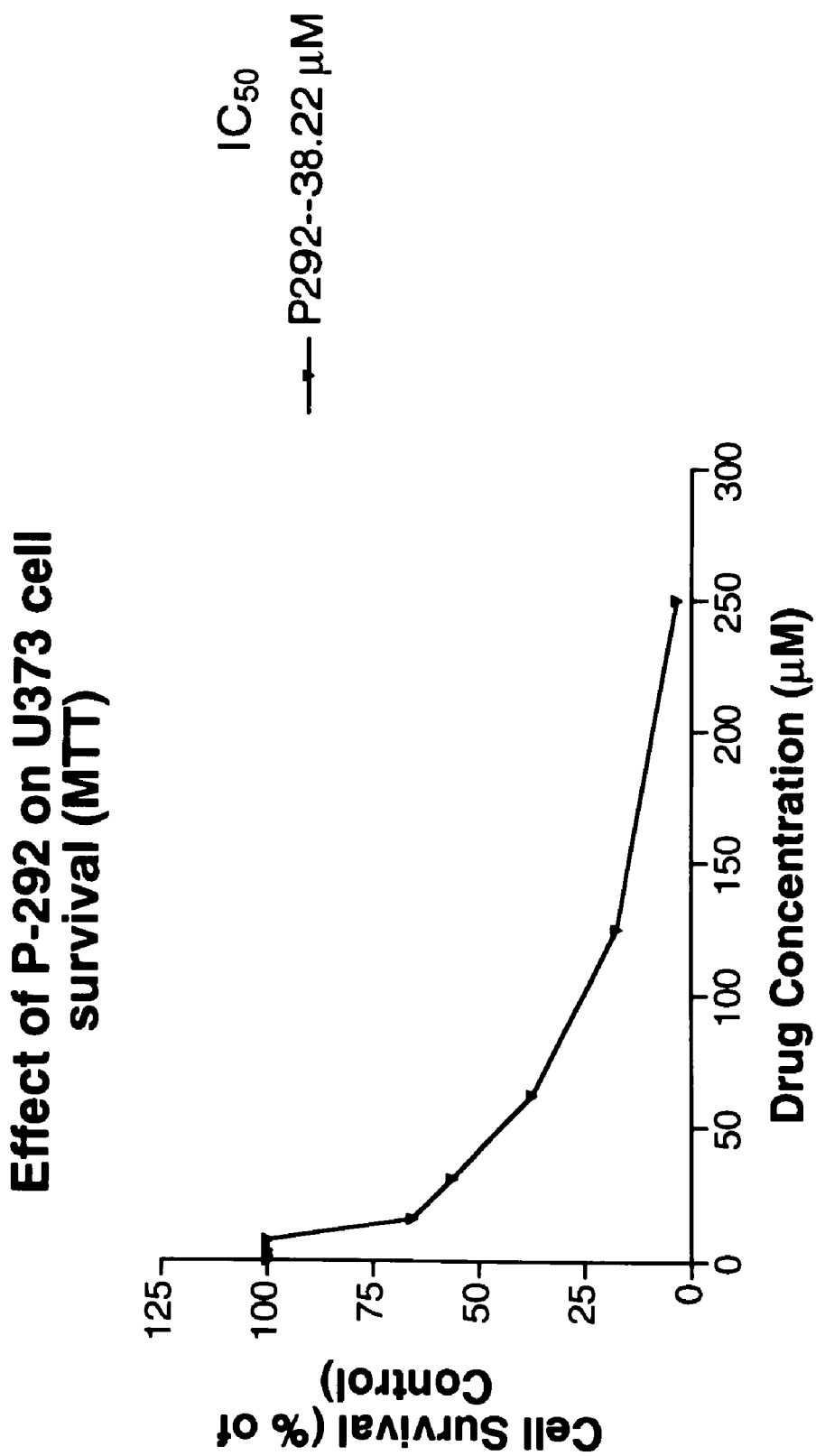
FIG. 15 is a graph demonstrating the cytotoxic effect of WHI-P292 on glioblastoma cells.

The novel compound WHI-P292 was assayed for cytotoxic activity in the MTT cell survival assay, as described above for Example 3. As shown in FIG. 15, this compound demonstrated potent cytotoxic activity against glioblastoma cells, with an $IC_{50}$ of 38.22 $\mu$M.

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A compound having the structural formula:

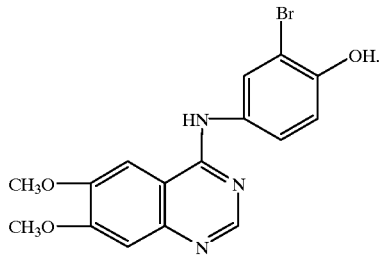

2. A compound having the structural formula:

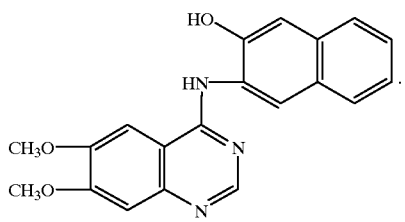

3. A compound having the structural formula:

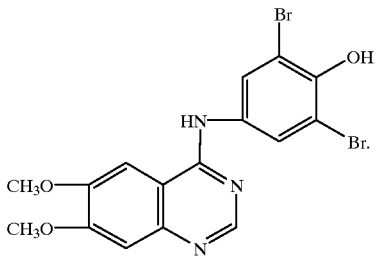

4. A composition comprising the compound according to claim 1 and an isotonic carrier.

5. A composition comprising the compound according to claim 2 and an isotonic carrier.

6. A method for inducing apoptosis of brain tumor cells, said method comprising contacting brain tumor cells with an effective apoptosis-inducing amount of a compound of the formula:

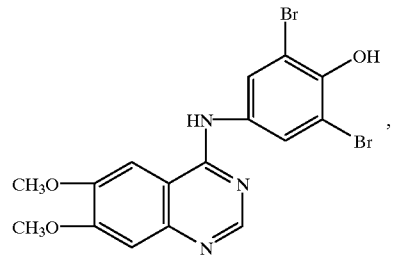

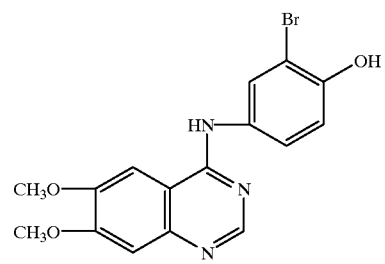

or a pharmaceutically acceptable acid addition salt thereof.

7. The method according to claim 6, wherein the compound has the formula:

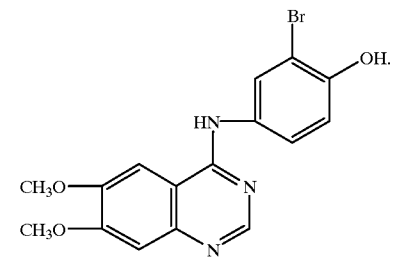

or a pharmaceutically acceptable acid addition salt thereof.

8. A method for preventing metastases of brain tumor cells, said method comprising contacting brain tumor cells with a compound of the formula:

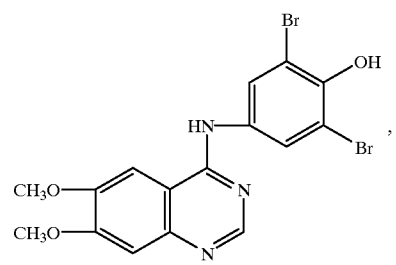

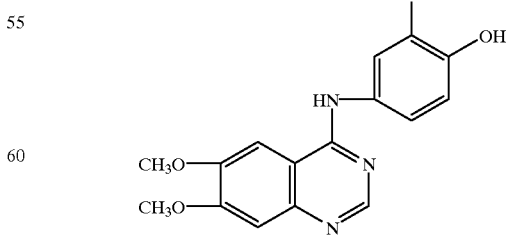

or a pharmaceutically acceptable acid addition salt thereof.

9. The method according to claim 8, wherein the compound has the formula:

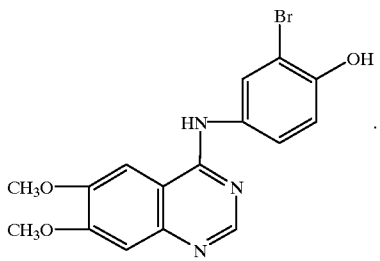

10. A method for inducing apoptosis of brain tumor cells, said method comprising contacting brain tumor cells with an effective apoptosis-inducing amount of a compound comprising the formulae:

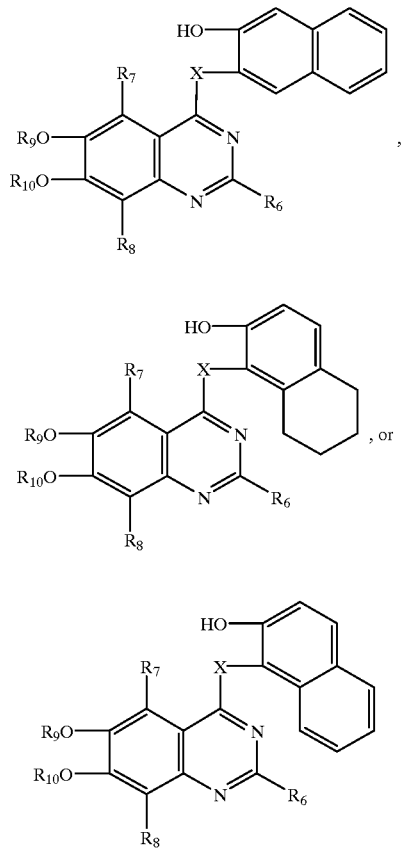

wherein X is HN;

$R_6$, $R_7$, and $R_8$ are the same or different and are each independently selected from the group consisting of H, OH, SH, $NH_2$, $NO_2$, halogen, alkoxy having up to four carbon atoms, alkylthio having up to four carbon atoms, and acyl wherein acyl is —C(O)R and R is H or alkyl having up to four carbon atoms; and $R_9$ and $R_{10}$ are the same or different and are each independently selected from the group consisting of H, alkyl having up to four carbon atoms, and acyl wherein acyl is —C(O)R and R is H or alkyl having up to four carbon atoms, or a pharmaceutically acceptable acid addition salt thereof;

or a pharmaceutically acceptable acid addition salt thereof.

11. The method according to claim 10, wherein the compound has the formula:

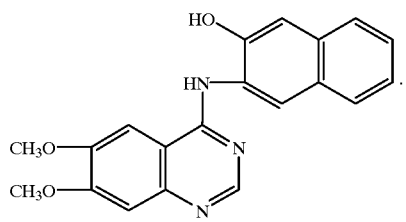

12. A method for preventing metastases of brain tumor cells, said method comprising contacting brain tumor cells with a compound of the formulae:

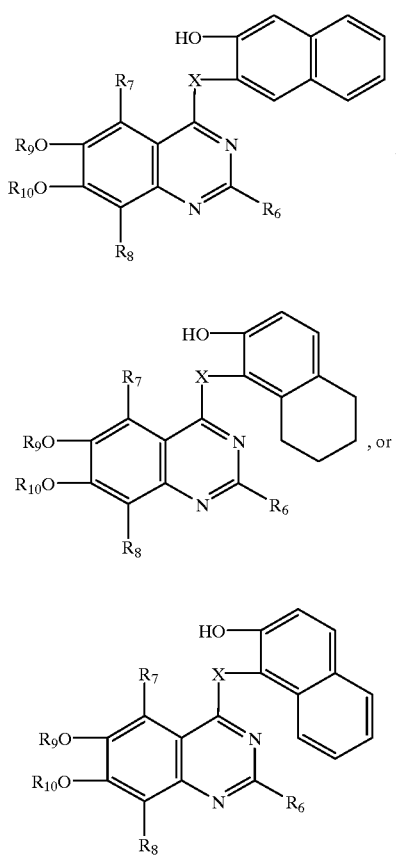

wherein X is HN;

$R_6$, $R_7$, and $R_8$ are the same or different and are each independently selected from the group consisting of H, OH, SH, $NH_2$, $NO_2$, halogen, alkoxy having up to four carbon atoms, alkylthio having up to four carbon atoms, and acyl wherein acyl is —C(O)R and R is H or alkyl having up to four carbon atoms; and $R_9$ and $R_{10}$ are the same or different and are each independently selected from the group consisting of H, alkyl having up to four carbon atoms, and acyl wherein acyl is —C(O)R and R is H or alkyl having up to four carbon atoms, or a pharmaceutically acceptable acid addition salt thereof;

or a pharmaceutically acceptable acid addition salt thereof.

13. The method of claim 12, wherein the compound has the formula:

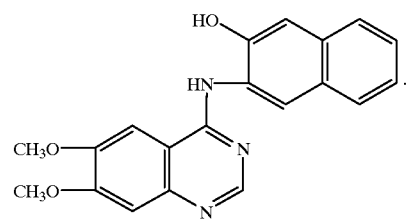

14. The method according to claim 6, wherein the compound has the structural formula:

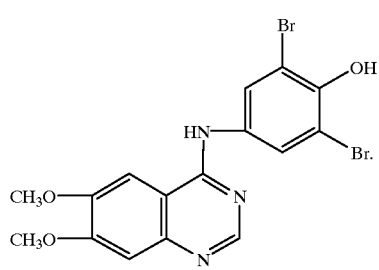

15. The method according to claim 8, wherein the compound has the structural formula:

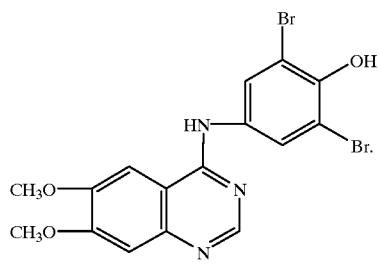

* * * * *